US012582661B2

(12) United States Patent
Peng et al.

(10) Patent No.: US 12,582,661 B2
(45) Date of Patent: *Mar. 24, 2026

(54) SYNTHESIS AND APPLICATION OF CLASS OF RESPIRATORY SYNCYTIAL VIRUS INHIBITORS

(71) Applicant: SHANGHAI ARK BIOPHARMACEUTICAL CO., LTD., Shanghai (CN)

(72) Inventors: Cheng Peng, Suzhou (CN); Xiashi Lv, Suzhou (CN); Mengfei Qian, Suzhou (CN); Wei Yin, Suzhou (CN); Chaojun Gong, Suzhou (CN); Jian Han, Suzhou (CN); Wei Shen, Suzhou (CN); Danbin Li, Suzhou (CN); Gang Zou, Suzhou (CN); Haiqing Yuan, Suzhou (CN); Zhen Jim Wu, Suzhou (CN)

(73) Assignee: SHANGHAI ARK BIOPHARMACEUTICAL CO., LTD., Shanghai (CN)

( * ) Notice: Subject to any disclaimer, the term of this patent is extended or adjusted under 35 U.S.C. 154(b) by 809 days.

This patent is subject to a terminal disclaimer.

(21) Appl. No.: 17/790,987

(22) PCT Filed: Jan. 21, 2021

(86) PCT No.: PCT/CN2021/073042

§ 371 (c)(1),
(2) Date: Jul. 6, 2022

(87) PCT Pub. No.: WO2021/147947

PCT Pub. Date: Jul. 29, 2021

(65) Prior Publication Data

US 2023/0090060 A1 Mar. 23, 2023

(30) Foreign Application Priority Data

Jan. 22, 2020 (CN) ......................... 202010075139.8

(51) Int. Cl.
*A61K 31/554* (2006.01)
*A61P 31/14* (2006.01)

(52) U.S. Cl.
CPC ............ *A61K 31/554* (2013.01); *A61P 31/14* (2018.01)

(58) Field of Classification Search
CPC ........ A61K 31/554; A61P 11/00; A61P 31/12; A61P 31/14; C07D 417/04; C07D 417/14
See application file for complete search history.

(56) References Cited

U.S. PATENT DOCUMENTS

| | | | |
|---|---|---|---|
| 5,760,230 A | 6/1998 | Schohe-Loop et al. | |
| 2023/0090060 A1 * | 3/2023 | Peng .................... | C07D 417/14 514/211.04 |

FOREIGN PATENT DOCUMENTS

| | | | | |
|---|---|---|---|---|
| CN | 103717589 A | 4/2014 | | |
| CN | 106414436 A | 2/2017 | | |
| CN | 108290882 A | 7/2018 | | |
| CN | 113149977 A | 7/2021 | | |
| JP | 2014521709 A | 8/2014 | | |
| WO | WO-2013020993 A1 * | 2/2013 | .............. | A61P 11/00 |
| WO | 2017009316 A1 | 1/2017 | | |

OTHER PUBLICATIONS

Mazur et. al., "Severe respiratory syncytial virus infection in children: burden, management, and emerging therapies", Lancet, 404 (Year: 2024).*
Meanwell, "Fluorine and Fluorinated Motifs in the Design and Application of Bioisosteres for Drug Design", Journal of Medicinal Chemistry, 61, 5822-5880 (Year: 2018).*
Xiufang Zheng et al., "Discovery of Ziresovir as a Potent, Selective, and Orally Bioavailable Respiratory Syncytial Virus Fusion Protein Inhibitor" J. Med. Chem. 2019, 62, 6003-6014 (Jun. 13, 2019).
Harshani R. Lawrence et al., "Development of Novel ACK1/TNK2 Inhibitors Using a Fragment-Based Approach" J. Med. Chem. 2015, 58, 2746-2763 (Feb. 20, 2015).
Ethan L. Fisher et al., "2,2,2-Trifluoroethoxy Aromatic Heterocycles: Hydrolytically Stable Alternatives to Heteroaryl Chlorides" J. Org. Chem. 2019, 84, 4904-4909 (Oct. 19, 2018).

* cited by examiner

*Primary Examiner* — Jeffrey H Murray
*Assistant Examiner* — Daniel John Burkett
(74) *Attorney, Agent, or Firm* — SZDC Law PC

(57) ABSTRACT

The present disclosure provides the synthesis and application of respiratory syncytial virus inhibitor, being a compound of formula I or a pharmaceutically acceptable salt, ester, isomer, solvate, prodrug or isotope label thereof.

I

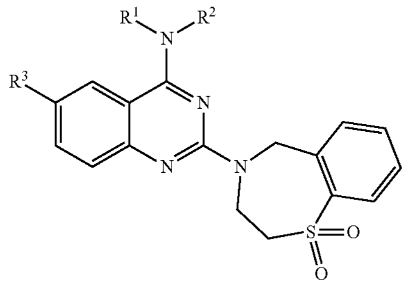

Compared with the existing inhibitors, the compounds of formula I have the advantages of superior activity and higher exposure in vivo.

11 Claims, No Drawings

SYNTHESIS AND APPLICATION OF CLASS OF RESPIRATORY SYNCYTIAL VIRUS INHIBITORS

CROSS-REFERENCE TO RELATED APPLICATION(S)

The present application is the national stage application of PCT/CN2021/073042, filed on Jan. 21, 2021, which claims the priority to the Chinese patent application NO. 202010075139.8, entitled "synthesis and application of respiratory syncytial virus inhibitors" which was filed on Jan. 22, 2020, and the disclosure of which is incorporated herein by reference in its entirety.

TECHNICAL FIELD

The present disclosure relates to the field of compounds, specifically to tetrahydrobenzo[1,4]thiazepine 1,1-dioxide compounds and the mixtures or compositions containing the same, especially the tetrahydrobenzo[1,4]thiazepine 1,1-dioxide compounds and the mixtures or compositions containing the same for the treatment and prophylaxis of respiratory syncytial virus.

TECHNICAL BACKGROUND

Respiratory syncytial virus (RSV) is an enveloped virus belonging to the *Streptococcus pneumoniae*. The RSV genome consists of 10 genes encoding 11 proteins: non-structural protein 1 and 2 (NS1 and NS2), nucleoprotein (N), phosphoprotein (P), matrix protein (M), small hydrophobic protein (SH), fusion protein (F), attachment glycoprotein (G), RNA-dependent RNA polymerase (L) and transcription anti-terminator protein (M2-1) and protein M2-2. RSV is a major cause of hospital admission for acute lower respiratory tract infection in young children. Each year, there are 33.8 million RSV-associated children under 5 years old globally, of which 3.4 million hospital admissions for acute lower respiratory tract infection (Ramagopal G., et al., *Journal of Clinical and Diagnostic Research,* 2016, 10(8): SC05-SC08).

Despite intensive research into RSV replication, pathogenesis and transmission, no vaccine has yet been approved. Palivizumab and ribavirin are currently approved drugs for the prevention and treatment of RSV, which are clinically recommended for high-risk patients with RSV infection, however its effectiveness in improving outcomes is questionable (Glick A. F., et al., *Hospital Pediatrics,* 2017, 7 (5): 271-278).

Currently, a number of small-molecule inhibitors against RSV infection have been discovered. According to the different mechanisms of drug-virus and drug-host interactions, these inhibitors can be divided into RSV virus-inactivating agents, RSV replication/protein synthesis inhibitors, RSV cells binding inhibitors, RSV cell invasion inhibitors, and host cell regulators of apoptosis, etc. These antiviral drugs are in different phases of clinical research (Villenave R. et al., *J. Virol.,* 2015, 89 (24): 12309-12318). For example, Alios BioPharma's nucleic acid analog ALS-8176 can terminate RNA chain synthesis, inhibit polymerization effect of L protein, and can reduce respiratory syncytial virus load in more than 85% of volunteers; Gilead's oral RSV fusion inhibitor GS-5806 can decrease viral load, mucus quantity and symptom scores. A class of RSV inhibitors was reported in WO2013020993, among which the representative Example 61-1 compound can inhibit the replication of RSV by blocking virus entry and cell fusion.

Although substantial progress has been made in the research of several drugs and monoclonal antibodies with different mechanisms of action for inhibiting RSV replication, the two antiviral drugs currently in clinical use are still insufficient to prevent and treat RSV infection, and there are no approved small molecule drugs. The drugs in clinical stages are in poor activity in inhibiting RSV replication and have a low exposure in vivo. Thus, RSV inhibitors have broad market prospects and huge therapeutic space, new inhibitors with superior activity and higher exposure in vivo for RSV infection are still needed urgently.

SUMMARY OF THE DISCLOSURE

Problems to be Solved

To solve the above technical problems, the present disclosure provides an RSV inhibitor with superior activity and higher exposure in vivo.

Solutions

To solve the above technical problems, the present disclosure provides the following solutions:

A compound of formula I or a pharmaceutically acceptable salt, ester, isomer, solvate, prodrug or isotope label thereof,

I

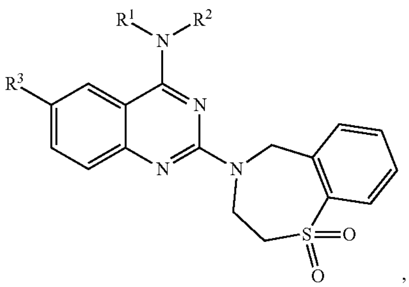

, wherein:

$R^1$ and $R^2$ are each independently selected from hydrogen, deuterium, and unsubstituted or $R^4$-substituted $C_{1-6}$ alkyl, $C_{3-7}$ cycloalkyl and 3 to 7 membered heterocyclyl, preferably unsubstituted or $R^4$-substituted $C_{1-6}$ alkyl, $C_{3-7}$ cycloalkyl and 3 to 7 membered heterocyclyl; or $R^1$ and $R^2$ are together to form a 3 to 6 membered heterocyclyl, wherein the 3 to 6 membered heterocyclyl is unsubstituted or substituted by $R^5$ and $R^6$;

$R^3$ is selected from halogen, carboxyl, $C_{1-6}$ alkyl, $C_{1-6}$ alkoxy and $C_{3-7}$ cycloalkyl, wherein the $C_{1-6}$ alkyl, $C_{1-6}$ alkoxy and $C_{3-7}$ cycloalkyl are unsubstituted or substituted with deuterium, halogen, hydroxyl and $C_{1-6}$ alkoxy, preferably halogen, carboxyl, $C_{1-6}$ alkyl and $C_{3-7}$ cycloalkyl, wherein the $C_{1-6}$ alkyl and $C_{3-7}$ cycloalkyl are unsubstituted or substituted with deuterium, halogen, hydroxyl and $C_{1-6}$ alkoxy;

Each of $R^4$ is independently selected from deuterium, hydroxyl, amino, cyano, halogen, $C_{1-6}$ alkyl, $C_{3-7}$ cycloalkyl and 3 to 6 membered heterocyclyl, wherein the $C_{1-6}$ alkyl, $C_{3-7}$ cycloalkyl and 3 to 6 membered heterocyclyl are unsubstituted or substituted with hydroxy, amino, cyano and halogen, preferably deuterium, hydroxy, amino, cyano, halogen, $C_{3-7}$ cycloalkyl and 3 to 6 membered heterocyclyl, wherein the $C_{3-7}$ cycloalkyl and 3 to 6 membered heterocyclyl are unsubstituted or substituted with hydroxy, amino, cyano and halogen;

$R^5$ and $R^6$ are each independently selected from hydrogen, deuterium, hydroxy, amino, cyano, halogen and $C_{1-6}$ alkyl, wherein the $C_{1-6}$ alkyl is unsubstituted or substituted with hydroxy, amino, cyano and halogen;

And that when $R^3$ is methyl, preferably when $R^1$ is hydrogen, $R^3$ is methyl, $R^2$ is not unsubstituted azetidine; and when $R^2$ is methylene, $R^3$ is methyl, preferably when $R^1$ is hydrogen, $R^2$ is methylene and $R^3$ is methyl, $R^4$ which is attached to $R^2$ is not an amino-substituted oxetanyl.

In one aspect, the present disclosure provides a pharmaceutical composition comprising the formula I compound or a pharmaceutically acceptable salt, ester, isomer, solvate, prodrug or isotope label thereof, and a use of the formula I compound and the pharmaceutical composition thereof in the preparation of medicaments for the prevention and/or treatment of diseases caused by respiratory syncytial virus infection, or use thereof as medicaments for the prevention and/or treatment of diseases caused by respiratory syncytial virus infection. In another aspect, the present disclosure also provides a method for preventing and/or treating diseases caused by respiratory syncytial virus infection, comprising a step of administering to a subject in need thereof a therapeutically effective amount of a compound of formula I, or a pharmaceutically acceptable salt, ester, isomer, solvate, prodrug or isotope label thereof, or a pharmaceutical composition containing the compound thereof.

Beneficial Effects of the Disclosure

Compared with the existing RSV inhibitors, the compounds disclosed herein have the advantages of superior activity and higher exposure in vivo.

DETAILED DESCRIPTION OF THE DISCLOSURE

To describe the content of the disclosure more clearly, the terms used in this application are defined as follows:

"$C_{1-6}$ alkyl" alone or in combination refers to a saturated straight chain or branched chain alkyl groups having 1 to 6 carbon atoms, preferably 1 to 4 carbon atoms, including methyl, ethyl, n-propyl, iso-propyl, butyl, sec-butyl, isobutyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, etc. Preferably, "$C_{1-6}$ alkyl" is selected from any one of methyl, ethyl, iso-propyl and tert-butyl.

"$C_{3-7}$ cycloalkyl" alone or in combination refers to a saturated cycloalkyl group having 3 to 7 carbon atoms, preferably 3 to 6 carbon atoms, including cyclopropyl, cyclobutyl, cyclopentyl, cyclohexyl and cycloheptyl, etc. Preferably, "$C_{3-7}$ cycloalkyl" is selected from any one of cyclopropyl, cyclopentyl and cyclohexyl.

"Heterocyclyl" alone or in combination refers to a saturated or partially unsaturated (having 1 or 2 double bond) non-aromatic cyclic group which is monocyclic or bicyclic consisting of carbon atoms and heteroatoms such as nitrogen, oxygen or sulfur. In the present disclosure, the heterocyclyl has 2 to 11 carbon atoms, and preferably has 1, 2, 3 or 4 heteroatoms, and the nitrogen, carbon or sulfur atom in the heterocyclyl can be optionally oxidized. The hydrogen atoms in the "heterocyclyl" are independently optionally substituted with one or more substituents described in the disclosure. "Heterocyclyl" can be linked to the parent molecule through any ring atom in the ring. "3 to 6 membered heterocyclyl" and "3 to 7 membered heterocyclyl" each independently refer to a saturated and/or partially unsaturated monocyclic or polycyclic group having 3 to 6 and 3 to 7 ring atoms including carbon atom and heteroatom, wherein the heteroatom is selected from N, O, $S(O)_m$ (wherein m is an integer from 0 to 2). Examples include aziridinyl, azetidinyl, oxetanyl, tetrahydropyrrolyl, tetrahydrofuranyl, tetrahydrothienyl, piperidinyl, morpholinyl, piperazinyl, thiomorpholinyl, tetrahydropyranyl, 1,1-dioxothiomorpholinyl and

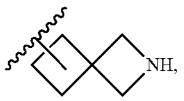

etc.

"$C_{1-6}$ alkoxy" alone or in combination refers to $C_{1-6}$ alkyl-O—, wherein "$C_{1-6}$ alkyl" is as defined above.

"Amino" alone or in combination refers to a primary amino group (—$NH_2$), a secondary amino group (—NH—) or a tertiary amino group ().

"Hydroxyl" alone or in combination refers to an —OH group.

"Halogen" alone or in combination refers to fluoro, chloro, bromo or iodo atoms, preferably fluoro, chloro or bromo atoms.

"Cyano" alone or in combination refers to a —CN group.

"Carboxyl" alone or in combination refers to a —COOH group.

"Isomer" means all isomeric forms including enantiomers, diastereomers and geometric isomers including cis- and trans-isomers. Therefore, the specific stereoisomeric forms of the compounds of the present disclosure or mixtures of enantiomers, diastereomers or geometric isomers (or cis-/trans-isomers) thereof are within the present disclosure.

"Pharmaceutically acceptable salt(s)" refers to the existing form of pharmaceutically acceptable salt of the compound of the disclosure, including acid addition salt and base addition salt. Pharmaceutically acceptable salt(s) are described by S. M. Berge et al. in J. Pharmaceutical Sciences (Vol. 66, p. 1-19, 1977) in the section "Pharmaceutical salts". In the present disclosure, pharmaceutically acceptable non-toxic acid addition salts are those formed with organic or inorganic acids, including but not limited to hydrochloric acid, sulfuric acid, hydrobromic acid, hydroiodic acid, phosphoric acid, nitric acid, perchloric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid and malic acid, etc. Pharmaceutically acceptable non-toxic base addition salts mean salts are those formed with organic or inorganic bases, including but not limited to alkali metal salts such as lithium, sodium or potassium salts; alkaline earth metal salts such as calcium or magnesium salts; organic base salts, such as ammonium salts or $N^+(C_{1-6}\ alkyl)_4$ salts formed with organic bases containing N groups. "Pharmaceutically acceptable salt(s)" can be synthesized by conventional chemical methods.

"Ester" means an ester derived by reacting one or more hydroxyl groups in a compound of the present disclosure with one or more protic acids selected from carboxylic acid, phosphoric acid, carbonic acid, sulfonic acid and boric acid, etc., or by reacting one or more carboxyl groups in a compound of the present disclosure with alcohols and/or phenols.

"Solvate" refers to an association of one or more solvent molecules with a compound of the present disclosure, wherein solvent molecules include, but are not limited to, water, methanol, ethanol, isopropanol, ethyl acetate, tetrahydrofuran, N,N-dimethylformamide, dimethyl sulfoxide, and the like.

"Hydrate" refers to the association of water with a compound of the present disclosure.

"Prodrug" refers to a derivative of a compound of the present disclosure that can be transformed in vivo to yield the formula I compound by a chemical reaction.

"Isotope label" refers to isotopic derivatives derived by substituting 1 to 6 deuterium atoms for hydrogen atoms in formula I and/or isotopes derived by replacing carbon atoms in formula I with 1 to 3 $^{14}C$ atoms.

The terms used in the present disclosure are as defined above, and those skilled in the art can also combined those with the prior art, and the content of the present disclosure is further described below based on the definitions.

The present disclosure provides a compound of formula I or a pharmaceutically acceptable salt, ester, isomer, solvate, prodrug or isotopic label thereof,

I

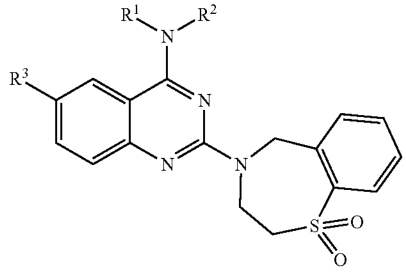

, wherein:

$R^1$ and $R^2$ are each independently selected from hydrogen, deuterium, and unsubstituted or $R^4$-substituted $C_{1-6}$ alkyl, $C_{3-7}$ cycloalkyl and 3 to 7 membered heterocyclyl, preferably unsubstituted or $R^4$-substituted $C_{1-6}$ alkyl, $C_{3-7}$ cycloalkyl and 3 to 7 membered heterocyclyl; or $R^1$ and $R^2$ are together to form a 3 to 6 membered heterocyclyl, wherein the 3 to 6 membered heterocyclyl is unsubstituted or substituted by $R^5$ and $R^6$; $R^5$ and $R^6$ are identical or different, and each of $R^5$ and $R^6$ is independently one or more.

$R^3$ is selected from halogen, carboxyl, $C_{1-6}$ alkyl, $C_{1-6}$ alkoxy and $C_{3-7}$ cycloalkyl, wherein the $C_{1-6}$ alkyl, $C_{1-6}$ alkoxy and $C_{3-7}$ cycloalkyl are unsubstituted or substituted with deuterium, halogen, hydroxyl and $C_{1-6}$ alkoxy, preferably halogen, carboxyl, $C_{1-6}$ alkyl and $C_{3-7}$ cycloalkyl, wherein the $C_{1-6}$ alkyl and $C_{3-7}$ cycloalkyl are unsubstituted or substituted with deuterium, halogen, hydroxyl and $C_{1-6}$ alkoxy;

Each of $R^4$ is independently selected from deuterium, hydroxyl, amino, cyano, halogen, $C_{1-6}$ alkyl, $C_{3-7}$ cycloalkyl and 3 to 6 membered heterocyclyl, wherein the $C_{1-6}$ alkyl, $C_{3-7}$ cycloalkyl and 3 to 6 membered heterocyclyl are unsubstituted or substituted with hydroxy, amino, cyano and halogen, preferably deuterium, hydroxy, amino, cyano, halogen, $C_{3-7}$ cycloalkyl and 3 to 6 membered heterocyclyl, wherein the $C_{3-7}$ cycloalkyl and 3 to 6 membered heterocyclyl are unsubstituted or substituted with hydroxy, amino, cyano and halogen;

$R^5$ and $R^6$ are each independently selected from hydrogen, deuterium, hydroxy, amino, cyano, halogen and $C_{1-6}$ alkyl, wherein the $C_{1-6}$ alkyl is unsubstituted or substituted with hydroxy, amino, cyano and halogen;

And when $R^3$ is methyl, preferably when $R^1$ is hydrogen, $R^3$ is methyl, $R^2$ is not unsubstituted azetidine; and when $R^2$ is methylene, $R^3$ is methyl, preferably when $R^1$ is hydrogen, $R^2$ is methylene and $R^3$ is methyl, $R^4$ which is attached to $R^2$ is not an amino-substituted oxetanyl.

$R^1$ is selected from hydrogen and deuterium, and $R^2$ is selected from unsubstituted or $R^4$-substituted methyl, ethyl, n-propyl, iso-propyl, cyclobutyl, cyclopentyl, cyclohexyl, tetrahydrofuranyl, tetrahydropyrrolyl, azetidinyl and

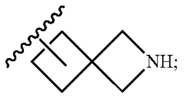

;

or $R^1$ and $R^2$ are together to form azetidinyl or tetrahydropyrrolyl, wherein the azetidinyl or tetrahydropyrrolyl are unsubstituted or substituted by $R^5$ and $R^6$.

In one preferred embodiment, $R^3$ is selected from methyl, deuterated methyl, cyclopropyl, fluoromethyl, trifluoromethyl, difluoromethoxy, trifluoromethoxy, carboxyl, 1-hydroxyethyl, 1-ethoxyethyl, 2-hydroxy-2-propyl and difluoromethyl.

$R^1$ and $R^2$ are each independently selected from hydrogen, deuterium, and $C_{1-6}$ alkyl, $C_{3-7}$ cycloalkyl and 3 to 7 membered heterocyclyl unsubstituted or substituted with one or two $R^4$, preferably $C_{1-6}$ alkyl, $C_{3-7}$ cycloalkyl and 3 to 7 membered heterocycloalkyl unsubstituted or substituted with one or two $R^4$. Each of $R^4$ is independently selected from deuterium, halogen, $C_{1-6}$ alkyl, cyano, amino, aminomethyl, hydroxy, hydroxymethyl, tetrahydropyrrolyl, oxetanyl, azetidinyl and cyclobutanyl, wherein the tetrahydropyrrolyl, oxetanyl, azetidinyl and cyclobutanyl are optionally substituted with hydroxy or amino, preferably deuterium, halogen, $C_{1-6}$ alkyl, cyano, amino, aminomethyl, hydroxy, hydroxymethyl, tetrahydropyrrolyl, azetidinyl and cyclobutanyl, wherein the tetrahydropyrrolyl, azetidinyl and cyclobutanyl are optionally substituted with hydroxy or amino.

In one preferred embodiment, $R^5$ and $R^6$ are each independently selected from hydrogen, hydroxy, amino, cyano, halogen, methyl, ethyl, n-propyl and iso-propyl, preferably hydroxy, amino, cyano, halogen, methyl, ethyl, n-propyl and iso-propyl; wherein the methyl, ethyl, n-propyl and iso-propyl are unsubstituted or substituted with hydroxy, amino and halogen.

In one preferred embodiment, $R^1$ is selected from hydrogen and deuterium, $R^2$ is selected from unsubstituted or $R^4$-substituted methyl, ethyl, n-propyl, iso-propyl, cyclobutyl, cyclopentyl, cyclohexyl, tetrahydrofuranyl, tetrahydropyrrolyl, azetidinyl and

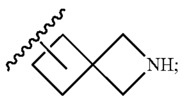

or $R^1$ and $R^2$ are together to form azetidinyl or tetrahydropyrrolyl, wherein the azetidinyl or tetrahydropyrrolyl is unsubstituted or substituted by $R^5$ and $R^6$;

Each of $R^4$ is independently selected from deuterium, hydroxy, amino, cyano, halogen and $C_{3-7}$ cycloalkyl, wherein the $C_{3-7}$ cycloalkyl is unsubstituted or substituted with hydroxy, amino and halogen;

Each of $R^5$ and $R^6$ is independently selected from hydrogen, hydroxy, amino, cyano, halogen, methyl, ethyl, n-propyl and iso-propyl, preferably hydroxy, amino, cyano, halogen, methyl, ethyl, n-propyl and iso-propyl, wherein the methyl, ethyl, n-propyl and iso-propyl are unsubstituted or substituted with hydroxy, amino and halogen.

In one preferred embodiment, $R^1$ is selected from hydrogen and deuterium, and $R^2$ is selected from unsubstituted or $R^4$-substituted methyl, ethyl cyclobutyl, cyclopentyl, cyclohexyl, tetrahydropyrrolyl, azetidinyl and

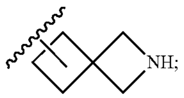

or $R^1$ and $R^2$ are together to form azetidinyl or tetrahydropyrrolyl, wherein the azetidinyl or tetrahydropyrrolyl is unsubstituted or substituted by $R^5$ and $R^6$;

Each of $R^4$ is independently selected from deuterium, hydroxy, amino, cyano and cyclobutyl, wherein the cyclobutyl is substituted by amino;

Each of $R^5$ and $R^6$ is independently selected from hydrogen, hydroxy, amino, methyl and ethyl, preferably hydroxy, amino, methyl and ethyl, wherein the methyl and ethyl are substituted by hydroxy and amino.

In one preferred embodiment, the compound of formula I is a compound of formula I-1:

I-1

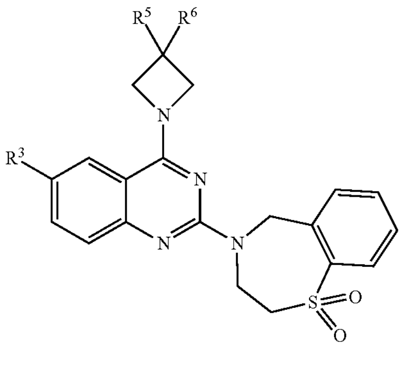

, wherein:

$R^3$ is methyl or difluoromethyl, $R^5$ and $R^6$ are each independently selected from hydrogen, deuterium, hydroxyl, amino, cyano, halogen and $C_{1-6}$ alkyl, wherein the $C_{1-6}$ alkyl is unsubstituted or substituted with deuterium, hydroxy, amino, cyano and halogen, and $R^5$ and $R^6$ are not both hydrogen or deuterium.

In one preferred embodiment, $R^5$ and $R^6$ are each independently selected from hydrogen, hydroxy, amino, cyano, methyl and ethyl, wherein the methyl and ethyl are substituted with hydroxy and amino, and $R^5$ and $R^6$ are not both hydrogen.

The present disclosure also provides a compound or a pharmaceutically acceptable salt, ester, isomer, solvate, prodrug or isotope label thereof, wherein the compound is selected from:

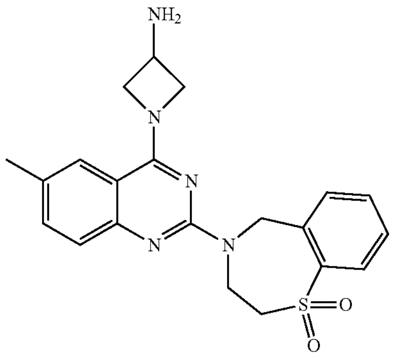

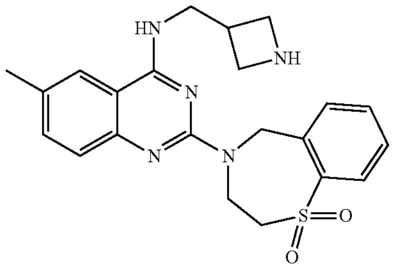

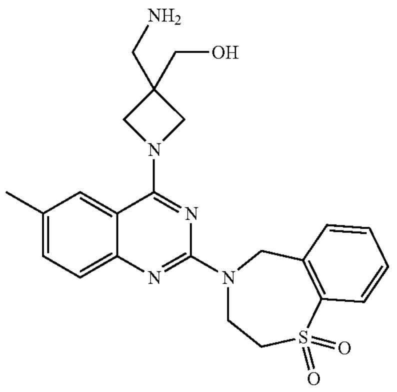

-continued
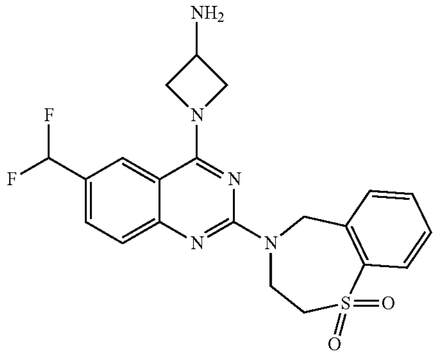
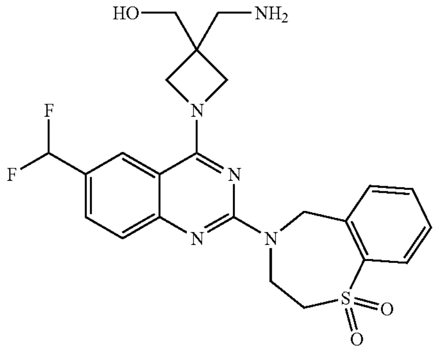
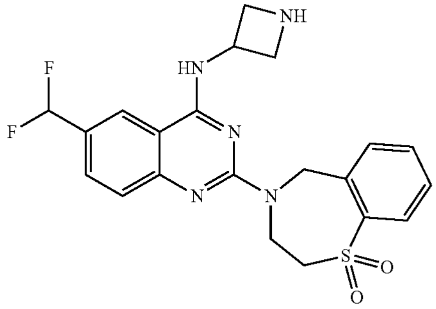
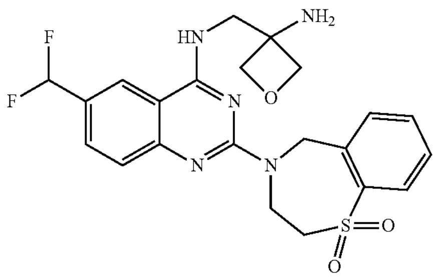
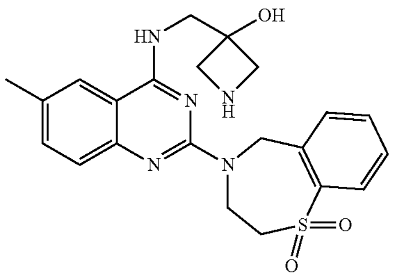
-continued
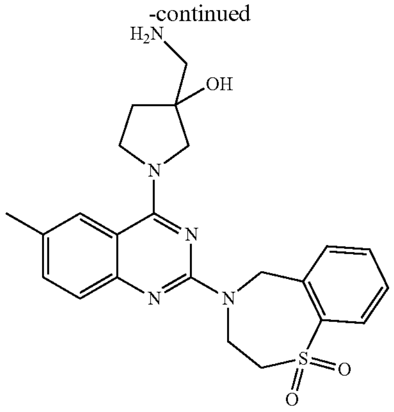
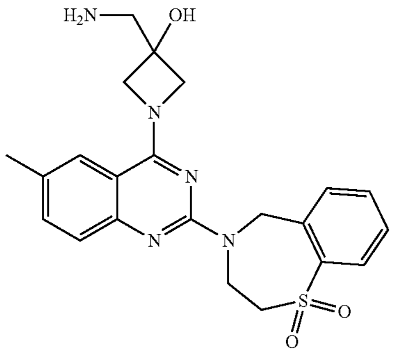
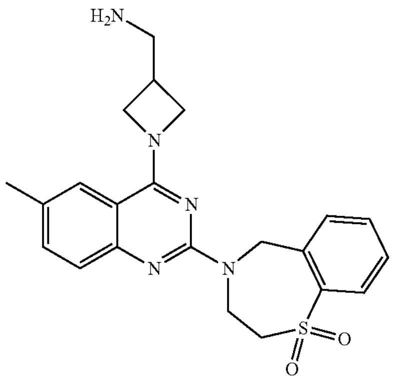
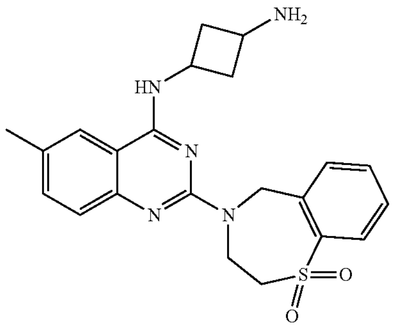

-continued

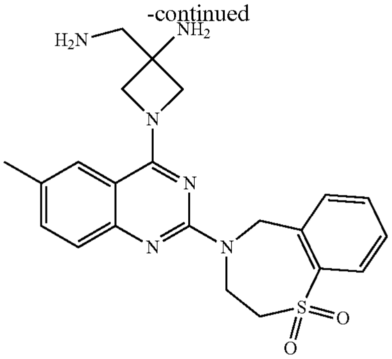

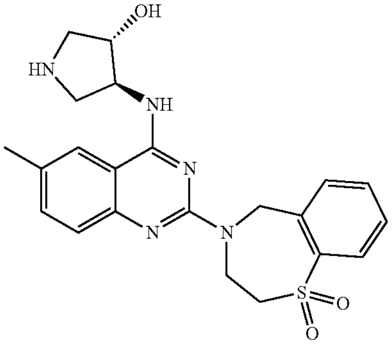

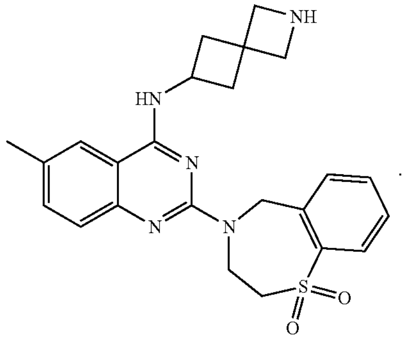

In one aspect, the present disclosure provides a pharmaceutical composition comprising the formula I compound or a pharmaceutically acceptable salt, ester, isomer, solvate, prodrug or isotope label thereof.

In one aspect, the present disclosure provides the use of the formula I compound or a pharmaceutically acceptable salt, ester, isomer, solvate, prodrug or isotope label thereof, or the pharmaceutical composition thereof in the preparation of medicaments for the prevention and/or treatment of diseases caused by respiratory syncytial virus infection.

In one aspect, the present disclosure provides the formula I compound or a pharmaceutically acceptable salt, ester, isomer, solvate, prodrug or isotope label thereof, or the pharmaceutical composition thereof, for use as a medicament for the prevention and/or treatment of diseases caused by respiratory syncytial virus infection.

In another aspect, the present disclosure also provides a method for preventing and/or treating diseases caused by respiratory syncytial virus infection, comprising a step of administering to a subject in need thereof a therapeutically effective amount of a compound of formula I, or a pharmaceutically acceptable salt, ester, isomer, solvate, prodrug or isotope label thereof, or a pharmaceutical composition containing the compound thereof.

The technical scheme of the present disclosure is further described by a typical synthetic route of the compound of formula I, which is specifically shown below:

Compound 1 gives compound 2 in the presence of sodium hydroxide;

Compound 2 reacts with compound 7 in the presence of triethylamine to give compound 3;

Compound 3 gives compound 4 in the presence of phosphorus oxychloride;

Compound 4 reacts with compound 8 in the presence of 1,8-diazabicyclo[5.4.0]undec-7-ene to give compound 5;

Compound 5 gives compound 6 by removing the protecting group in the presence of trifluoroacetic acid.

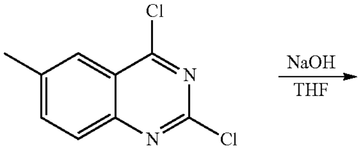

1

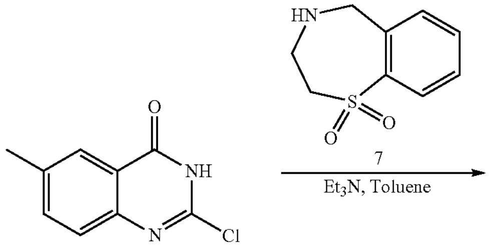

7

2

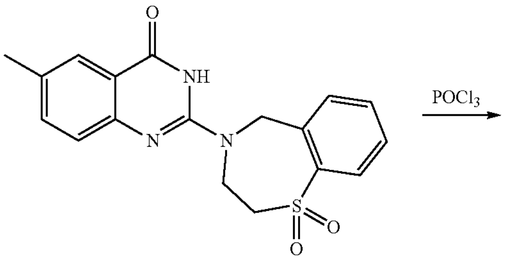

3

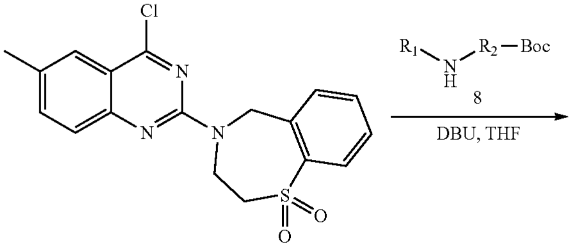

8

4

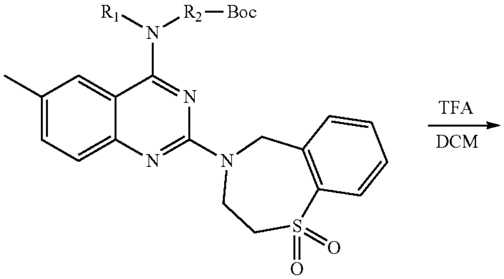

5

-continued

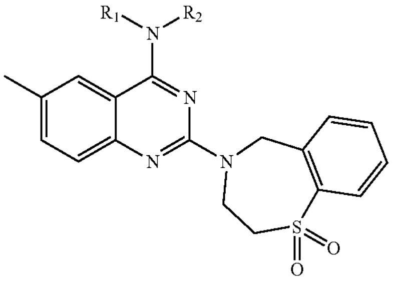

6

As a variation of the above typical synthetic route, another reaction route is shown below: when $R^3$ is difluoromethyl, the reaction route of compounds 9 to 12 refers to the typical synthetic route of compound 1 to 4, and the following only describes a partial reaction scheme from compound 12.

The compound 12 reacts with trifluoroethanol to obtain the target compound 13 in the presence of potassium tert-butoxide;

Compound 13 reacts with compound 18 in the presence of n-butyllithium to obtain compound 14;

Compound 14 gives compound 15 in the presence of DAST;

Compound 15 reacts with compound 19 in the presence of triethylamine to obtain the compound 16;

Compound 16 gives compound 17 by removing the protecting group in the presence of trifluoroacetic acid.

The reaction route is as follows:

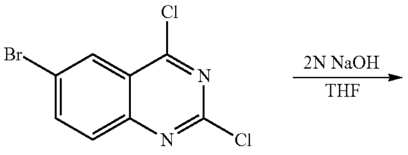

9

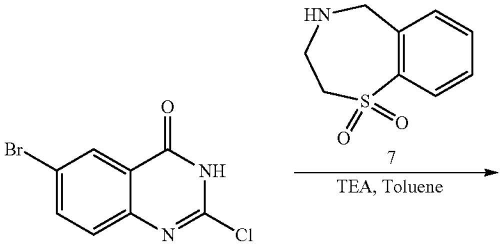

10

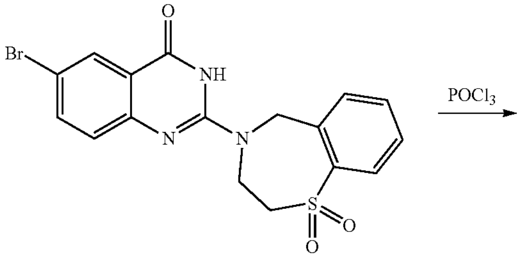

11

-continued

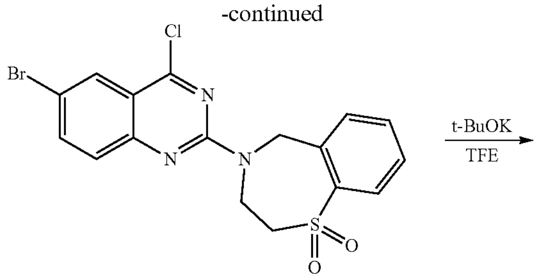

12

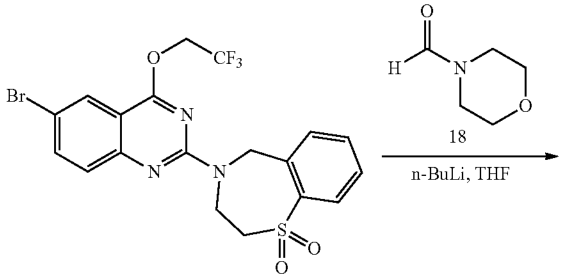

13

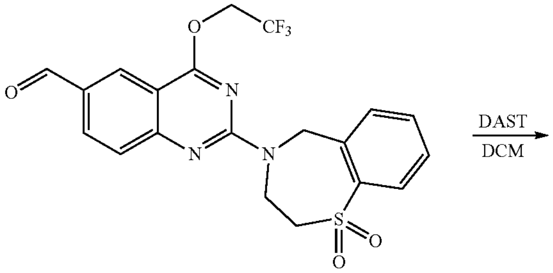

14

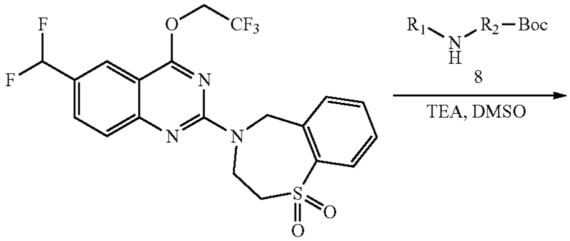

15

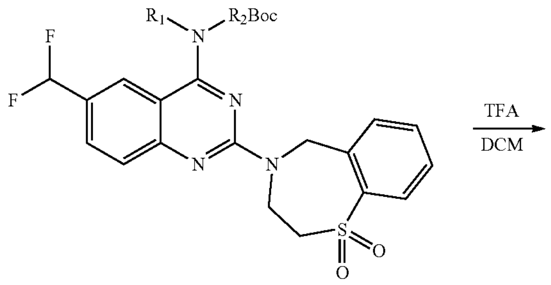

16

-continued

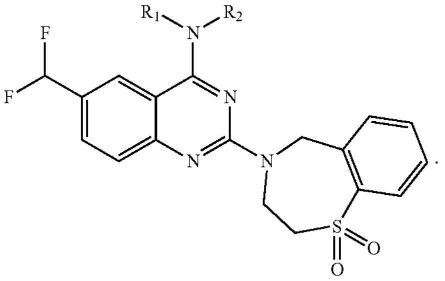

17

Another variable reaction scheme is shown below:

Compound 19 reacts with NBS in the presence of AIBN to obtain compound 20;

Compound 20 reacts with compound 26 in the presence of triethylamine to obtain compound 21;

Compound 21 reacts with silver nitrate to obtain compound 22;

Compound 22 reacts with DAST to obtain compound 23;

Compound 23 reacts with compound 7 in the presence of ammonium chloride to obtain compound 24;

Compound 24 gives compound 25 by removing the protecting group in the presence of trifluoroacetic acid.

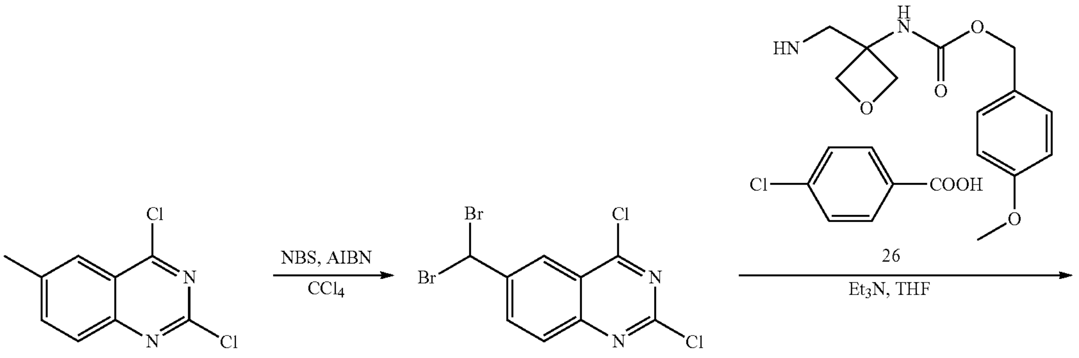

19 20

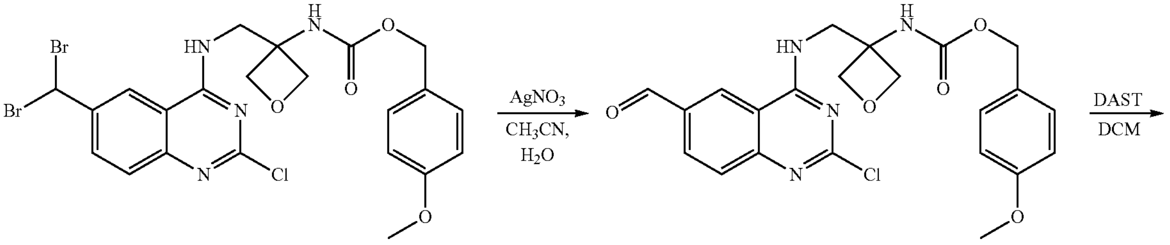

21 22

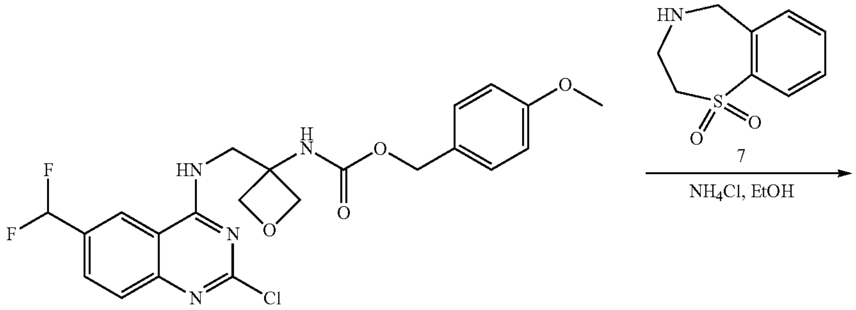

23

-continued

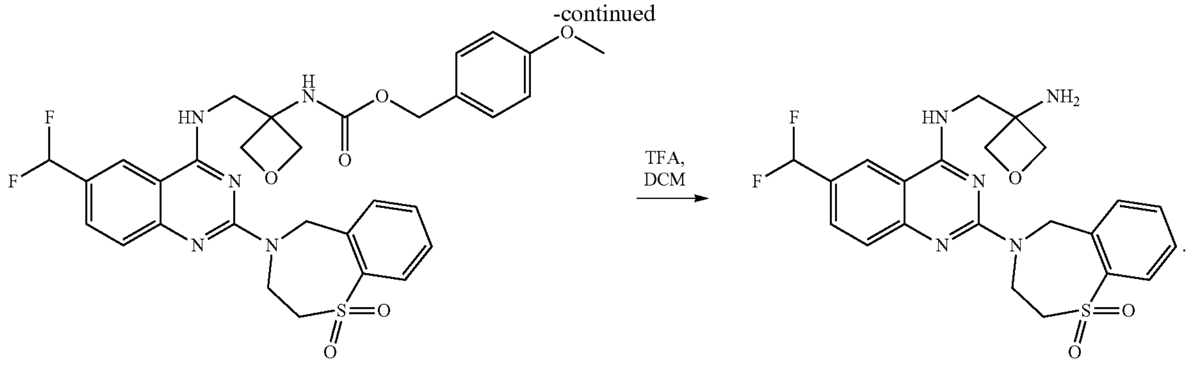

24 25

The following examples serve to illustrate the disclosure, but the examples should not be considered as limiting the scope of the present disclosure.

The following abbreviations are used in this application:

$CCl_4$ is carbon tetrachloride, $CDCl_3$ is deuterated chloroform, $CC_{50}$ is concentration cytotoxicity 50%, $CO_2$ is carbon dioxide, DAST is diethylaminosulfur trifluoride, DBU is 1,8-diazabicyclo[5.4.0]undec-7-ene, DMF is N,N-dimethylformamide, DMSO-d6 is deuterated dimethyl sulfoxide G is grams, HCOOH is formic acid, Hz is hertz, h is hours, $IC_{50}$ is half maximal inhibitory concentration, mg is milligrams, mL is milliliter, mmol is millimoles, MHz is megahertz, $NaHCO_3$ is sodium bicarbonate, NBS is N-bromosuccinimide, NMR is nuclear magnetic resonance, M is molarity, PyBOP is benzotriazol-1-yl-oxytripyrrolidinophosphonium hexafluorophosphate, TLC is thin layer chromatography, μM is micromol/liter, μg is microgram, μL is microliter, δ is chemical shift.

Specific conditions for the experimental method in the examples of the present disclosure are generally as follows:

First, unless otherwise stated in the examples, the following reactions were placed under nitrogen atmosphere.

Further, intermediates and final compounds were separated and purified by Column chromatography, Preparative chromatography and ICSO rapid preparative chromatography system.

Further, the LC-MS chromatograph was generally performed on Waters ACQUITY Arc equipped with QDa Detector. Mass spectrometry (MS) uses an ESI source and only indicates the molecular weight M of the parent molecule, usually reporting $[M+H]^+$.

Injection volume was determined by sample concentration; flow rate: 0.8 mL/min; HPLC peaks were read by recording UV-Vis wavelengths at 220 nm and 254 nm.

The mobile phases were 0.01% formic acid in ultrapure water (mobile phase A) and 0.01% formic acid in acetonitrile (mobile phase B). The gradient elution conditions are shown in the following Table 1 and Table 2:

TABLE 1

| gradient elution condition 1 | | |
|---|---|---|
| Time(min) | A($H_2O$, 0.01% HCOOH) | B($CH_3CN$, 0.01% HCOOH) |
| 0.0-0.3 | 95-85 | 5-15 |
| 0.3-3.2 | 85-20 | 15-80 |
| 3.2-3.8 | 20-5 | 80-95 |
| 3.8-3.81 | 5-95 | 95-5 |
| 3.81-4.0 | 95 | 5 |

TABLE 2

| gradient elution condition 2 | | |
|---|---|---|
| Time(min) | A($H_2O$, 0.01% HCOOH) | B($CH_3CN$, 0.01% HCOOH) |
| 0.00-5.90 | 95-5 | 5-95 |
| 5.90-5.91 | 5-95 | 95-5 |
| 5.91-6.00 | 95 | 5 |

Further, NMR spectra were obtained using a Varian 400 MHz nuclear magnetic resonance. The solvents were usually $CDCl_3$ and DMSO-$d_6$, and the chemical shifts were given in ppm. The various peaks are described as follows: s (singlet), d (doublet), t (triplet), q (quartet), m (multiplet), dd (doublet doublet). Coupling constants are indicated in Hz.

Example 1

4-(4-(3-Aminoazetidin-1-yl)-6-methylquinazolin-2-yl)-2,3,4,5-tetrahydrobenzo[f][1,4]thiazepine 1,1-dioxide

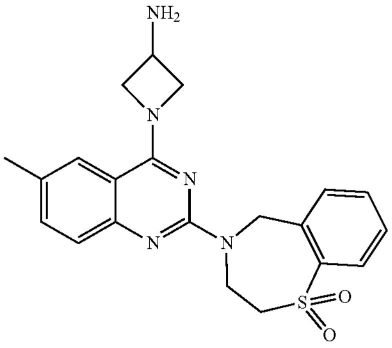 [SMILES: Cc1ccc2nc(N3CCS(=O)(=O)c4ccccc4C3)nc(N3CC(N)C3)c2c1]

Step 1a

2-Chloro-6-methylquinazolin-4(3H)-one

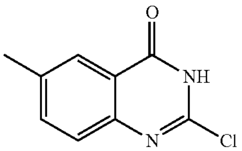

To a solution of 2,4-dichloro-6-methylquinazoline (8.0 g, 37.55 mmol) in tetrahydrofuran (80 mL) was added 2 M aqueous sodium hydroxide solution (20 mL) at room temperature. The mixture was stirred at room temperature for 8 hours. Then, acetic acid (20 mL) was added dropwise to the reaction mixture, followed by suction filtration, and the filter cake was washed with ethyl acetate (20 mL). The filter cake was dried under reduced pressure to obtain 2-chloro-6-methylquinazolin-4(3H)-one (7.0 g) as a white solid.

Step 1b 2-(1,1-Dioxido-2,3-dihydrobenzo[f][1,4]thiazepin-4(5H)-yl)-6-methylquinazolin-4(3H)-one

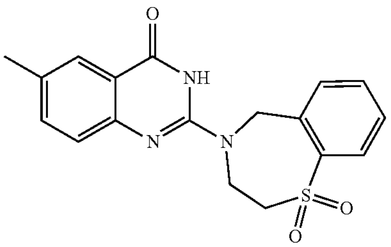 [SMILES: Cc1ccc2nc(N3CCS(=O)(=O)c4ccccc4C3)[nH]c(=O)c2c1]

To a solution of 2-chloro-6-methylquinazolin-4(3H)-one (7.0 g, 35.97 mmol) in toluene (150 mL) were added 2,3,4,5-tetrahydrobenzo[1,4]thiazepine 1,1-dioxide (9.22 g, 46.76 mmol) and triethylamine (10 mL) at room temperature. The mixture was stirred at 130° C. for 10 hours.

It was then suction filtered, and the filter cake was washed with ethyl acetate (30 mL). The filter cake was dried under reduced pressure to obtain a white solid 2-(1,1-dioxido-2,3-dihydrobenzo[f][1,4]thiazepin-4(5H)-yl)-6-methylquinazolin-4(3H)-one (11.5 g).

Step 1c 4-(4-Chloro-6-methylquinazolin-2-yl)-2,3,4,5-tetrahydrobenzo[f][1,4]thiazepine 1,1-dioxide

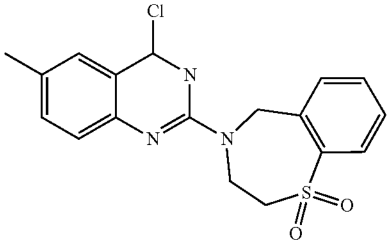 [SMILES: Cc1ccc2c(c1)C(Cl)NC(N1CCS(=O)(=O)c3ccccc3C1)=N2]

2-(1,1-dioxido-2,3-dihydrobenzo[f][1,4]thiazepin-4(5H)-yl)-6-methylquinazolin-4(3H)-one (1.5 g, 4.22 mmol) was added to phosphorus oxychloride (15 mL) in a nitrogen atmosphere at room temperature. The mixture was stirred at 80° C. for 2 hours and then cooled to room temperature. Phosphorus oxychloride was distilled off under reduced pressure, the residue was poured into ice water, and extracted with ethyl acetate (20 mL×2). The combined organic phases were washed with saturated brine (10 mL), dried over anhydrous sodium sulfate and filtered. The filtrate was concentrated at reduced pressure to obtain 4-(4-chloro-6-methylquinazolin-2-yl)-2,3,4,5-tetrahydrobenzo[f][1,4]thiazepine 1,1-dioxide as a yellow solid (1.58 g).

Step 1d

Tert-butyl (1-(2-(1,1-dioxido-2,3-dihydrobenzo[f][1,4]thiazepin-4(5H)-yl)-6-methylquinazolin-4-yl)azetidin-3-yl)carbamate

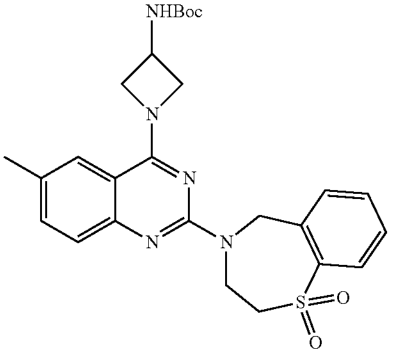 [SMILES: Cc1ccc2nc(N3CCS(=O)(=O)c4ccccc4C3)nc(N3CC(NC(=O)OC(C)(C)C)C3)c2c1]

In a nitrogen atmosphere, to a solution of 4-(4-chloro-6-methylquinazolin-2-yl)-2,3,4,5-tetrahydrobenzo[f][1,4]thiazepine 1,1-dioxide (108 mg, 0.29 mmol) and tert-butyl azetidine-3-ylcarbamate (100 mg, 0.58 mmol) in anhydrous tetrahydrofuran solution (10 mL) was added DBU (48 mg, 0.32 mmol) at room temperature. The mixture was stirred at reflux for 16 hours and then cooled to room temperature, diluted with ethyl acetate (20 mL) and washed with water (10 mL). The aqueous phase was extracted with ethyl acetate (20 mL×2). The combined organic phases were washed with saturated brine (10 mL), dried over anhydrous sodium sulfate and filtered. The filtrate was concentrated at reduced pressure to obtain a crude product. The crude product was purified by flash column chromatography to give tert-butyl (1-(2-(1,1-dioxido-2,3-dihydrobenzo[f][1,4]thiazepin-4(5H)-yl)-6-methylquinazolin-4-yl)azetidin-3-yl)carbamate as a white solid (125 mg).

Step 1e 4-(4-(3-Aminoazetidin-1-yl)-6-methylquinazolin-2-yl)-2,3,4,5-tetrahydrobenzo[f][1,4]thiazepine 1,1-dioxide

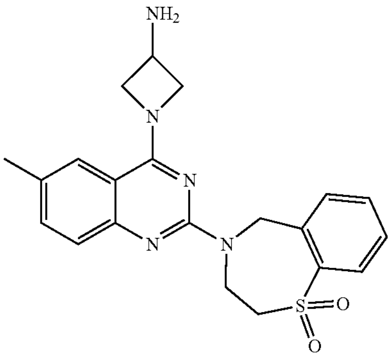 [SMILES: Cc1ccc2nc(N3CCS(=O)(=O)c4ccccc4C3)nc(N3CC(N)C3)c2c1]

To a solution of tert-butyl (1-(2-(1,1-dioxido-2,3-dihydrobenzo[f][1,4]thiazepin-4(5H)-yl)-6-methylquinazolin-4-yl)azetidin-3-yl)carbamate (125 mg, 0.25 mmol) in dichloromethane (4 mL) was added trifluoroacetic acid (1 mL) at room temperature. The mixture was stirred at room temperature for 2 hours, concentrated at reduced pressure to remove trifluoroacetic acid, and was adjusted pH to 8 with concentrated ammonia water, and then was concentrated under reduced pressure to obtain a crude product, and was purified through flash column chromatography to give 4-(4-(3-aminoazetidin-1-yl)-6-methylquinazolin-2-yl)-2,3,4,5-tetrahydrobenzo[f][1,4]thiazepine 1,1-dioxide as a white solid (65 mg).

$^1$H NMR (400 MHz, $CD_3OD$) δ7.95 (d, J=7.6 Hz, 1H), 7.83 (d, J=7.6 Hz, 1H), 7.58 (t, J=7.8 Hz, 1H), 7.48 (s, 1H), 7.42 (t, J=7.6 Hz, 1H), 7.38-7.29 (m, 2H), 5.15 (s, 2H), 4.73 (t, J=8.4 Hz, 2H), 4.52 (br. s, 2H), 4.23-4.15 (m, 2H), 4.03-3.94 (m, 1H), 3.49 (t, J=10.0 Hz, 2H), 2.35 (s, 3H).

MS (ESI+)[$(M+H)^+$]: 410.

Example 2

4-(4-((Azetidin-3-ylmethyl)amino)-6-methylquinazolin-2-yl)-2,3,4,5-tetrahydrobenzo[f][1,4]thiazepine 1,1-dioxide

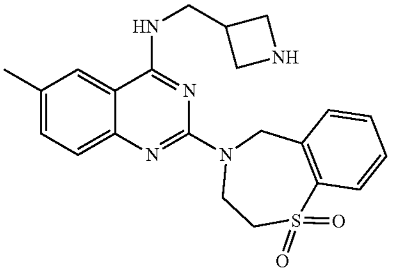 [SMILES: Cc1ccc2nc(N3CCS(=O)(=O)c4ccccc4C3)nc(NCC3CNC3)c2c1]

Step 2a tert-butyl 3-(((2-(1,1-dioxido-2,3-dihydrobenzo[f][1,4]thiazepin-4(5H)-yl)-6-methylquinazolin-4-yl)amino)methyl)azetidine-1-carboxylate

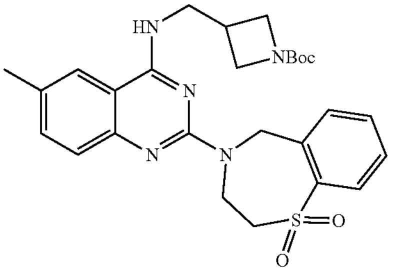 [SMILES: Cc1ccc2nc(N3CCS(=O)(=O)c4ccccc4C3)nc(NCC3CN(C(=O)OC(C)(C)C)C3)c2c1]

4-(4-Chloro-6-methylquinazolin-2-yl)-2,3,4,5-tetrahydrobenzo[f][1,4]thiazepine 1,1-dioxide (100 mg, 0.27 mmol) reacted with tert-butyl 3-(aminomethyl)azetidine-1-carboxylate (99 mg, 0.53 mmol) in a similar manner according to the preparing method depicted in Step 1d of Example 1, to give tert-butyl 3-(((2-(1,1-dioxido-2,3-dihydrobenzo[f][1,4]thiazepin-4(5H)-yl)-6-methylquinazolin-4-yl)amino)methyl)azetidine-1-carboxylate as a white solid (98 mg).

Step 2b 4-(4-((Azetidin-3-ylmethyl)amino)-6-methylquinazolin-2-yl)-2,3,4,5-tetrahydrobenzo[f][1,4]thiazepine 1,1-dioxide

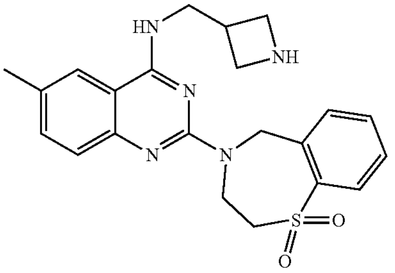 [SMILES: Cc1ccc2nc(N3CCS(=O)(=O)c4ccccc4C3)nc(NCC3CNC3)c2c1]

Tert-butyl 3-(((2-(1,1-dioxido-2,3-dihydrobenzo[f][1,4]thiazepin-4(5H)-yl)-6-methyl-quinazolin-4-yl)amino)methyl)azetidine-1-carboxylate (98 mg, 0.19 mmol) was subjected to a reaction in a similar manner according to the preparing method depicted in Step 1e of Example 1, to give 4-(4-((azetidine-3-ylmethyl)amino)-6-methylquinazolin-2-yl)-2,3,4,5-tetrahydro-benzo[f][1,4]thiazepine 1,1-dioxide (15.4 mg) as a white solid.

$^1$1H NMR (400 MHz, $CD_3OD$) δ 8.00 (d, J=7.6 Hz, 1H), 7.82 (d, J=7.6 Hz, 1H), 7.71 (s, 1H), 7.62 (t, J=7.2 Hz, 1H), 7.49-7.43 (m, 2H), 7.35 (t, J=8.4 Hz, 1H), 5.22 (br. s, 2H), 4.59 (s, 2H), 4.18-4.13 (m, 2H), 4.07-4.03 (m, 2H), 3.89 (d, J=6.0 Hz, 2H), 3.57 (t, J=5.0 Hz, 2H), 3.47-3.43 (m, 1H), 2.42 (s, 3H).

MS ($ESI^+$)[$(M+H)^+$]: 424.

Example 3

4-(4-(3-(Aminomethyl)-3-(hydroxymethyl)azetidin-1-yl)-6-methylquinazolin-2-yl)-2,3,4,5-tetrahydrobenzo[f][1,4]thiazepine 1,1-dioxide

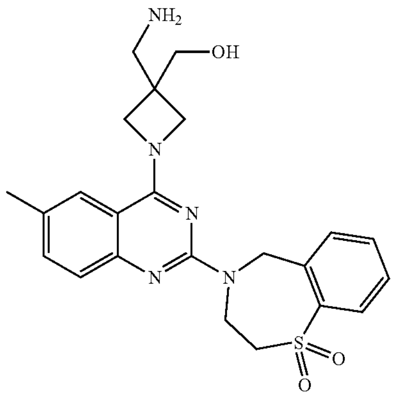 [SMILES: Cc1ccc2nc(N3CCS(=O)(=O)c4ccccc4C3)nc(N3CC(CN)(CO)C3)c2c1]

Step 3a tert-butyl ((1-(2-(1,1-dioxido-2,3-dihydrobenzo[f][1,4]thiazepin-4(5H)-yl)-6-methylquinazolin-4-yl)-3-(hydroxymethyl)azetidin-3-yl)methyl)carbamate

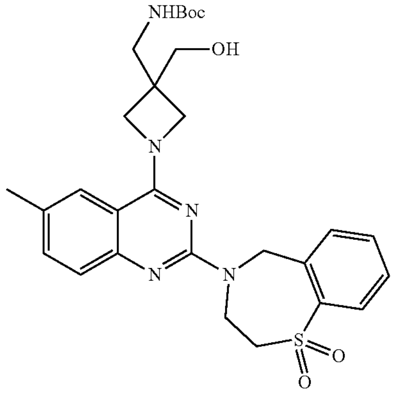 [SMILES: Cc1ccc2nc(N3CCS(=O)(=O)c4ccccc4C3)nc(N3CC(CO)(CNC(=O)OC(C)(C)C)C3)c2c1]

4-(4-Chloro-6-methylquinazolin-2-yl)-2,3,4,5-tetrahydrobenzo[f][1,4]thiazepine 1,1-dioxide (50 mg, 0.13 mmol) reacted with tert-butyl ((3-(hydroxymethyl)azetidin-3-yl)methyl)carbamate hydrochloride (34 mg, 0.13 mmol) in a similar manner according to the preparing method depicted in Step 1d of Example 1, to give tert-butyl ((1-(2-(1,1-dioxido-2,3-dihydrobenzo[f][1,4]thiazepin-4(5H)-yl)-6-methylquinazolin-4-yl)-3-(hydroxymethyl)azetidin-3-yl)methyl)carbamate as a white solid (60 mg).

Step 3b

4-(4-(3-(Aminomethyl)-3-(hydroxymethyl)azetidin-1-yl)-6-methylquinazolin-2-yl)-2,3,4,5-tetrahydrobenzo[f][1,4]thiazepine 1,1-dioxide

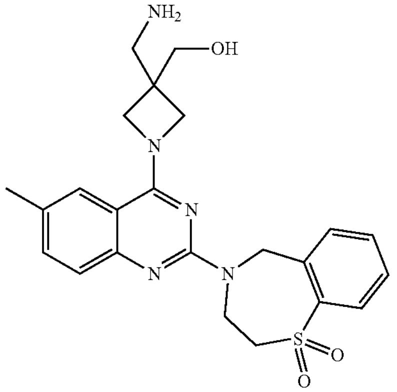 [SMILES: Cc1ccc2nc(N3CCS(=O)(=O)c4ccccc4C3)nc(N3CC(CN)(CO)C3)c2c1]

tert-butyl ((1-(2-(1,1-dioxido-2,3-dihydrobenzo[f][1,4]thiazepin-4(5H)-yl)-6-methyl-quinazolin-4-yl)-3-(hydroxymethyl)azetidin-3-yl)methyl)carbamate (30 mg, 0.05 mmol) was subjected to a reaction in a similar manner according to the preparing method depicted in Step 1e of Example 1, to give 4-(4-(3-(Aminomethyl)-3-(hydroxymethyl)azetidin-1-yl)-6-methylquinazolin-2-yl)-2,3,4,5-tetrahydrobenzo[f][1,4]thiazepine 1,1-dioxide (14 mg) as a white solid.

$^1$H NMR (400 MHz, DMSO-d6) δ 7.88 (d, J=8.0 Hz, 1H), 7.82-7.73 (m, 1H), 7.68-7.61 (m, 1H), 7.53-7.43 (m, 2H), 7.36 (d, J=8.0 Hz, 1H), 7.30-7.22 (m, 1H), 6.04 (br. s, 3H), 5.05 (br. s, 2H), 4.53-4.13 (m, 6H), 3.67 (s, 2H), 3.56 (s, 2H), 3.06 (s, 2H), 2.31 (s, 3H).

MS ($ESI^+$)[$(M+H)^+$]: 454.

Example 4

4-(4-(3-Aminoazetidin-1-yl)-6-(difluoromethyl)quinazolin-2-yl)-2,3,4,5-tetrahydrobenzo[f][1,4]thiazepine 1,1-dioxide

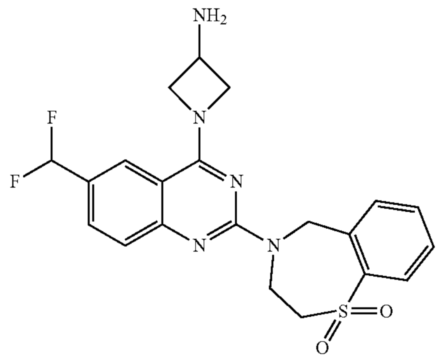 [SMILES: NC1CN(c2nc(N3CCS(=O)(=O)c4ccccc4C3)nc3ccc(C(F)F)cc23)C1]

Step 4a

6-Bromo-2-chloroquinazolin-4(3H)-one

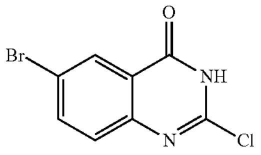 [SMILES: O=c1[nH]c(Cl)nc2ccc(Br)cc12]

6-Bromo-2,4-dichloroquinazoline (5.0 g, 18 mmol) was subjected to a reaction in a similar manner according to the preparing method depicted in Step 1a of Example 1, to give 6-bromo-2-chloroquinazoline-4(3H)-one (4.4 g) as a pale yellow solid.

Step 4b

6-Bromo-2-(1,1-dioxido-2,3-dihydrobenzo[f][1,4]thiazepin-4(5H)-yl)quinazolin-4(3H)-one

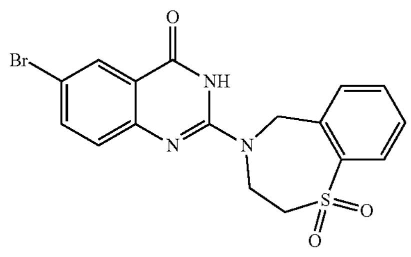 [SMILES: O=c1[nH]c(N2CCS(=O)(=O)c3ccccc3C2)nc2ccc(Br)cc12]

6-Bromo-2-chloroquinazolin-4(3H)-one (5.1 g, 19.6 mmol) reacted with 2,3,4,5-tetrahydrobenzo[1,4]thiazepine 1,1-dioxide (5.0 g, 25.6 mmol) in a similar manner according to the preparing method depicted in Step 1b of Example 1, to give 6-bromo-2-(1,1-dioxido-2,3-dihydrobenzo[f][1,4]thiazepin-4(5H)-yl)quinazolin-4(3H)-one (7.2 g) as a white solid.

Step 4c 4-(6-Bromo-4-chloroquinazolin-2-yl)-2,3,4,5-tetrahydrobenzo[f][1,4]thiazepine 1,1-dioxide

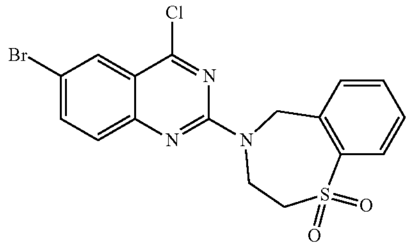 [SMILES: O=S1(=O)CCN(c2nc(Cl)c3cc(Br)ccc3n2)Cc2ccccc21]

6-Bromo-2-(1,1-dioxido-2,3-dihydrobenzo[f][1,4]thiazepin-4(5H)-yl)quinazolin-4(3H)-one (7.2 g, 17.1 mmol) was subjected to a reaction in a similar manner according to the preparing method depicted in Step 1c of Example 1, to give 4-(6-bromo-4-chloroquinazolin-2-yl)-2,3,4,5-tetrahydrobenzo[f][1,4]thiazepine 1,1-dioxide (5.3 g) as a yellow solid.

Step 4c 4-(6-Bromo-4-(2,2,2-trifluoroethoxy)quinazolin-2-yl)-2,3,4,5-tetrahydrobenzo[f][1,4]thiazepine 1,1-dioxide

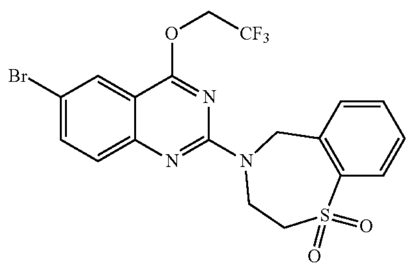 [SMILES: O=S1(=O)CCN(c2nc(OCC(F)(F)F)c3cc(Br)ccc3n2)Cc2ccccc21]

To a solution of 4-(6-bromo-4-chloroquinazolin-2-yl)-2,3,4,5-tetrahydro-benzo[f][1,4]thiazepine 1,1-dioxide (5.3 g, 12.1 mmol) in trifluoroethanol (100 mL), potassium tert-butoxide (2.7 g, 24.1 mmol) was added in a nitrogen atmosphere. The mixture was stirred at 60° C. for 4 hours and then cooled to room temperature, diluted with water (100 mL), and extracted with ethyl acetate (150 mL×3). The combined organic phases were washed with saturated brine (50 mL), dried over anhydrous sodium sulfate and filtered. The filtrate was concentrated under reduced pressure to obtain a crude product. The crude product was purified by flash column chromatography to give 4-(6-bromo-4-(2,2,2-trifluoroethoxy)quinazolin-2-yl)-2,3,4,5-tetrahydrobenzo[f][1,4]thiazepine 1,1-dioxide (5.0 g) as a yellow solid.

Step 4e 2-(1,1-dioxido-2,3-dihydrobenzo[f][1,4]thiazepin-4(5H)-yl)-4-(2,2,2-trifluoroethoxy)quinazoline-6-carbaldehyde

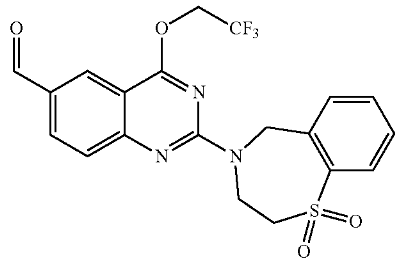 [SMILES: O=Cc1ccc2nc(N3CCS(=O)(=O)c4ccccc4C3)nc(OCC(F)(F)F)c2c1]

To a solution of 4-(6-bromo-4-(2,2,2-trifluoroethoxy)quinazolin-2-yl)-2,3,4,5-tetrahydrobenzo[f][1,4]thiazepine 1,1-dioxide and N-formylmorpholine (1.7 g, 14.9 mmol) in anhydrous tetrahydrofuran solution (30 mL), a solution of n-butyllithium (2.5 M, 4 mL, 10 mmol) was added dropwise for 2 hours at −40° C. in a nitrogen atmosphere. The mixture was further stirred at −40° C. for 1 hour, then the reaction was quenched with ammonium chloride (30 mL) solution at −40° C. and extracted with ethyl acetate (40 mL×3), then the combined organic phases were washed with saturated brine (30 mL), dried over anhydrous sodium sulfate and filtered. The filtrate was concentrated under reduced pressure to obtain a crude product. The crude product was purified by flash column chromatography to give 2-(1,1-dioxido-2,3-dihydrobenzo[f][1,4]thiazepin-4(5H)-yl)-4-(2,2,2-trifluoroethoxy)quinazoline-6-carbaldehyde as a yellow solid (600 mg).

Step 4f 4-(6-(Difluoromethyl)-4-(2,2,2-trifluoroethoxy)quinazolin-2-yl)-2,3,4,5-tetrahydrobenzo[f][1,4]thiazepine 1,1-dioxide

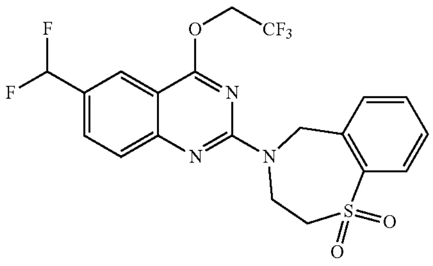 [SMILES: O=S1(=O)CCN(c2nc(OCC(F)(F)F)c3cc(C(F)F)ccc3n2)Cc2ccccc21]

To a solution of 2-(1,1-dioxido-2,3-dihydrobenzo[f][1,4]thiazepin-4(5H)-yl)-4-(2,2,2-trifluoroethoxy)quinazoline-6-carbaldehyde (500 mg, 1.1 mmol) in anhydrous dichloromethane (10 mL), diethylaminosulfur trifluoride (446 mg, 2.8 mmol) was added in a nitrogen atmosphere. The mixture was stirred at room temperature for 16 hours, then the reaction was quenched with saturated sodium bicarbonate (20 mL) solution, extracted with ethyl acetate (20 mL×3), and the combined organic phases were washed with saturated brine (20 mL), dried over anhydrous sodium sulfate and filtered. The filtrate was concentrated under reduced pressure to obtain a crude product. The crude product was purified by flash column chromatography to give 4-(6-(difluoromethyl)-4-(2,2,2-trifluoroethoxy)quinazolin-2-yl)-2,3,4,5-tetrahydrobenzo[f][1,4]thiazepine 1,1-dioxide (490 mg) as a pale yellow solid.

Step 4g

Tert-butyl (1-(6-(difluoromethyl)-2-(1,1-dioxido-2,3-dihydrobenzo[f][1,4]thiazepin-4(5H)-yl)quinazolin-4-yl)azetidin-3-yl)carbamate

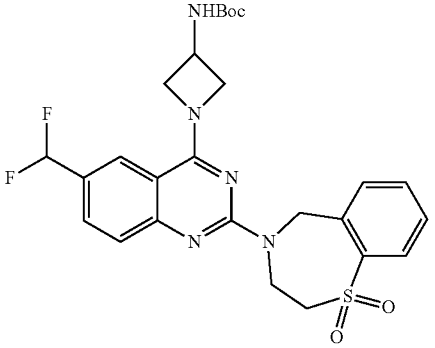 [SMILES: CC(C)(C)OC(=O)NC1CN(c2nc(N3CCS(=O)(=O)c4ccccc4C3)nc3ccc(C(F)F)cc23)C1]

To a solution of 4-(6-(difluoromethyl)-4-(2,2,2-trifluoroethoxy)quinazolin-2-yl)-2,3,4,5-tetrahydrobenzo[f][1,4]thiazepine 1,1-dioxide (50 mg, 0.10 mmol) and tert-butyl azetidin-3-ylcarbamate (27 mg, 0.16 mmol) in dimethyl sulfoxide (2 mL), triethylamine (32 mg, 0.32 mmol) was added. The mixture was stirred at 90° C. for 3 hours and then cooled to room temperature, diluted with ethyl acetate (30 mL), and washed with water (10 mL×3). The organic phase was washed with saturated brine (10 mL), dried over anhydrous sodium sulfate and filtered. The filtrate was concentrated under reduced pressure to obtain a crude product. The crude product was purified by flash column chromatography to give tert-butyl (1-(6-(difluoromethyl)-2-(1,1-dioxido-2,3-dihydrobenzo[f][1,4]thiazepin-4(5H)-yl)quinazolin-4-yl)azetidin-3-yl)carbamate (35 mg) as a white solid.

Step 4h 4-(4-(3-Aminoazetidin-1-yl)-6-(difluoromethyl)quinazolin-2-yl)-2,3,4,5-tetrahydrobenzo[f][1,4]thiazepine 1,1-dioxide

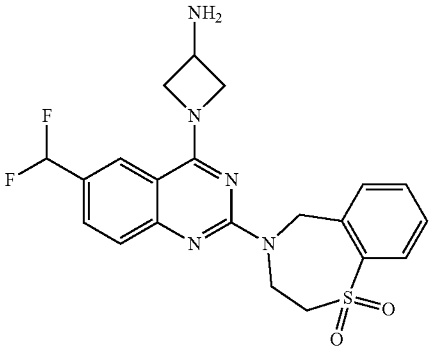 [SMILES: NC1CN(c2nc(N3CCS(=O)(=O)c4ccccc4C3)nc3ccc(C(F)F)cc23)C1]

Tert-butyl (1-(6-(difluoromethyl)-2-(1,1-dioxido-2,3-dihydrobenzo[f][1,4]thiazepin-4(5H)-yl)quinazolin-4-yl)azetidin-3-yl)carbamate (35 mg, 0.06 mmol) was subjected to a reaction in a similar manner according to the preparing method depicted in Step 1e of Example 1, to give 4-(4-(3-aminoazetidin-1-yl)-6-(difluoromethyl)quinazolin-2-yl)-2,3,4,5-tetrahydrobenzo[f][1,4]thiazepine 1,1-dioxide (16 mg) as a white solid.

$^1$H NMR (400 MHz, $CD_3OD$) δ 7.96 (d, J=7.6 Hz, 1H), 7.83 (s, 1H), 7.80 (d, J=7.6 Hz, 1H), 7.67-7.56 (m, 2H), 7.50-7.40 (m, 2H), 6.76 (t, J=56.4 Hz, 1H), 5.18 (br. s, 2H), 4.78 (br. s, 2H), 4.66-4.47 (m, 2H), 4.23 (br.s, 2H), 4.05-3.98 (m, 1H), 3.50 (t, J=5.2 Hz, 2H).

MS ($ESI^+$)[$(M+H)^+$]: 446.

Example 5

4-(4-(3-(Aminomethyl)-3-(hydroxymethyl)azetidin-1-yl)-6-(difluoromethyl)quinazolin-2-yl)-2,3,4,5-tetrahydrobenzo[f][1,4]thiazepine 1,1-dioxide

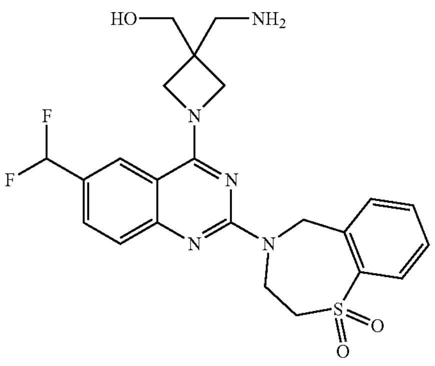 [SMILES: NCC1(CO)CN(c2nc(N3CCS(=O)(=O)c4ccccc4C3)nc3ccc(C(F)F)cc23)C1]

Step 5a

Tert-butyl ((1-(6-(difluoromethyl)-2-(1,1-dioxido-2,3-dihydrobenzo[f][1,4]thiazepin-4(5H)-yl)quinazolin-4-yl)-3-(hydroxymethyl)azetidin-3-yl)methyl) carbamate

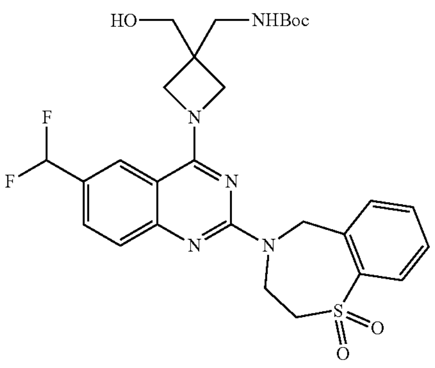 [SMILES: CC(C)(C)OC(=O)NCC1(CO)CN(c2nc(N3CCS(=O)(=O)c4ccccc4C3)nc3ccc(C(F)F)cc23)C1]

4-(6-(Difluoromethyl)-4-(2,2,2-trifluoroethoxy)quinazolin-2-yl)-2,3,4,5-tetrahydrobenzo[f][1,4]thiazepine 1,1-dioxide (50 mg, 0.10 mmol) reacted with tert-butyl ((3-(hydroxymethyl)azetidin-3-yl)methyl)carbamate (27 mg, 0.16 mmol) in a similar manner according to the preparing method depicted in step 4g in Example 4, to give tert-butyl ((1-(6-(difluoromethyl)-2-(1,1-dioxido-2,3-dihydrobenzo[f][1,4]thiazepin-4(5H)-yl)quinazolin-4-yl)-3-(hydroxymethyl)azetidin-3-yl)methyl)carbamate (35 mg) as a white solid.

Step 5b 4-(4-(3-(Aminomethyl)-3-(hydroxymethyl)azetidin-1-yl)-6-(difluoromethyl)quinazolin-2-yl)-2,3,4,5-tetrahydrobenzo[f][1,4]thiazepine 1,1-dioxide

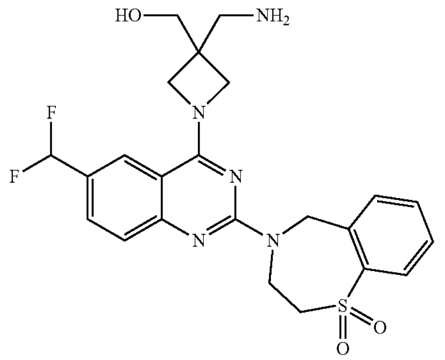 [SMILES: NCC1(CO)CN(c2nc(N3CCS(=O)(=O)c4ccccc4C3)nc3ccc(C(F)F)cc23)C1]

Tert-butyl ((1-(6-(difluoromethyl)-2-(1,1-dioxido-2,3-dihydrobenzo[f][1,4]thiazepin-4(5H)-yl)quinazolin-4-yl)-3-(hydroxymethyl)azetidin-3-yl)methyl)carbamate (35 mg, 0.06 mmol) was subjected to a reaction in a similar manner according to the preparing method depicted in Step 1e of Example 1, to give 4-(4-(3-(aminomethyl)-3-(hydroxymethyl)azetidin-1-yl)-6-(difluoromethyl)quinazolin-2-yl)-2,3,4,5-tetrahydrobenzo[f][1,4]thiazepine 1,1-dioxide (15 mg) as a white solid.

$^1$H NMR (400 MHz, $CD_3OD$) δ 7.96 (d, J=7.6 Hz, 1H), 7.86 (s, 1H), 7.81 (d, J=7.2 Hz, 1H), 7.65 (d, J=8.0 Hz, 1H), 7.60 (t, J=7.6 Hz, 1H), 7.49 (d, J=8.4 Hz, 1H), 7.44 (t, J=8.0 Hz, 1H), 6.77 (t, J=56.4 Hz, 1H), 5.19 (br. s, 2H), 4.68-4.24 (m, 6H), 3.95 (s, 2H), 3.50 (t, J=5.0 Hz, 2H), 3.42 (s, 2H).

MS ($ESI^+$)[$(M+H)^+$]: 490.

Example 6

4-(4-(Azetidin-3-ylamino)-6-(difluoromethyl)quinazolin-2-yl)-2,3,4,5-tetrahydrobenzo[f][1,4]thiazepine 1,1-dioxide

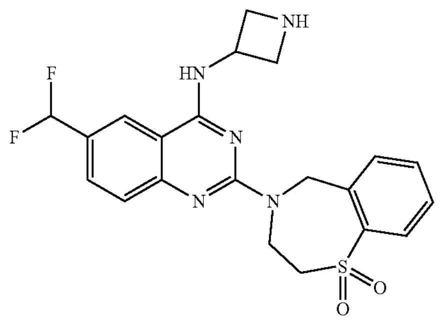 [SMILES: O=S1(=O)CCN(c2nc(NC3CNC3)c3cc(C(F)F)ccc3n2)Cc2ccccc21]

Step 6a

Tert-butyl 3-((6-(difluoromethyl)-2-(1,1-dioxido-2,3-dihydrobenzo[f][1,4]thiazepin-4(5H)-yl)quinazolin-4-yl)amino)azetidine-1-carboxylate

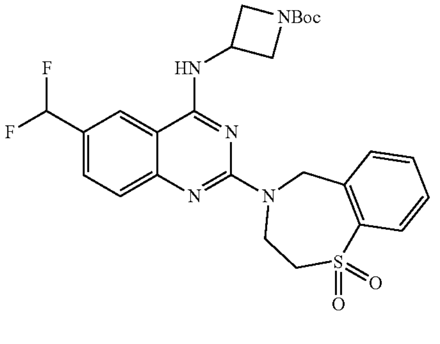 [SMILES: CC(C)(C)OC(=O)N1CC(Nc2nc(N3CCS(=O)(=O)c4ccccc4C3)nc3ccc(C(F)F)cc23)C1]

4-(6-(difluoromethyl)-4-(2,2,2-trifluoroethoxy)quinazolin-2-yl)-2,3,4,5-tetrahydrobenzo[f][1,4]thiazepine 1,1-dioxide (50 mg, 0.10 mmol) reacted with tert-butyl 3-aminoazetidine-1-carboxylate (37 mg, 0.21 mmol) in a similar manner according to the preparing method depicted in step 4g in Example 4, to give tert-butyl 3-((6-(difluoromethyl)-2-(1,1-dioxido-2,3-dihydrobenzo[f][1,4]thiazepin-4(5H)-yl)quinazolin-4-yl)amino)azetidine-1-carboxylate (24 mg) as a white solid.

Step 6b 4-(4-(Azetidin-3-ylamino)-6-(difluoromethyl)quinazolin-2-yl)-2,3,4,5-tetrahydrobenzo[f][1,4]thiazepine 1,1-dioxide

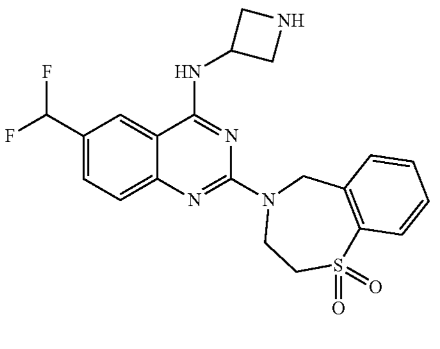 [SMILES: O=S1(=O)CCN(c2nc(NC3CNC3)c3cc(C(F)F)ccc3n2)Cc2ccccc21]

tert-butyl 3-((6-(difluoromethyl)-2-(1,1-dioxido-2,3-dihydrobenzo[f][1,4]thiazepin-4(5H)-yl)quinazolin-4-yl)amino)azetidine-1-carboxylate (24 mg, 0.04 mol) was subjected to a reaction in a similar manner according to the preparing method depicted in Step 1e of Example 1, to give 4-(4-(azetidin-3-ylamino)-6-(difluoromethyl)quinazolin-2-yl)-2,3,4,5-tetrahydrobenzo[f][1,4]thiazepine 1,1-dioxide (6.1 mg) as a white solid.

$^{1}$1H NMR (400 MHz, $CD_3OD$) δ 8.19 (s, 1H), 8.00 (d, J=7.6 Hz, 1H), 7.90 (d, J=7.6 Hz, 1H), 7.71 (d, J=9.2 Hz, 1H), 7.66 (s, 1H), 7.53 (d, J=9.2 Hz, 1H), 7.48 (t, J=7.8 Hz, 1H), 6.81 (t, J=56.2 Hz, 1H), 5.23 (br. s, 2H), 4.61 (br. s, 3H), 4.48 (br. s, 2H), 4.29-4.21 (m, 2H), 3.52 (t, J=4.6 Hz, 2H).

MS ($ESI^+$)[$(M+H)^+$]: 446.

Example 7

4-(4-(((3-Aminooxetan-3-yl)methyl)amino)-6-(difluoromethyl)quinazolin-2-yl)-2,3,4,5-tetrahydrobenzo[f][1,4]thiazepine 1,1-dioxide

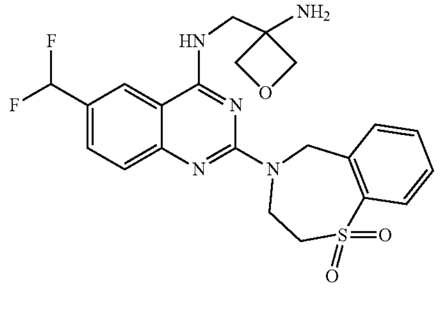 [SMILES: NC1(CNc2nc(N3CCS(=O)(=O)c4ccccc4C3)nc3ccc(C(F)F)cc23)COC1]

Step 7a 2,4-Dichloro-6-(dibromomethyl)quinazoline

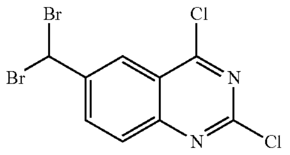 [SMILES: Clc1nc(Cl)c2cc(C(Br)Br)ccc2n1]

2,4-Dichloro-6-methyl-quinazoline (10 g, 46.9 mmol) was dissolved in $CCl_4$ (100 mL) at room temperature, NBS (33.4 g, 0.187 mol) and AIBN (1.93 mol, 11.7 mmol) were added in portions. Then the mixture was heated to 90° C. for 4 hours, and TLC showed the reaction was completed. The reaction solution was cooled to room temperature and washed with saturated $NaHCO_3$ solution and saturated brine. After concentration, the crude product was separated and purified by flash column chromatography to give 2,4-dichloro-6-(dibromomethyl)quinazoline (12 g) as a yellow solid.

Step 7b

4-Methoxybenzyl (3-(((2-chloro-6-(dibromomethyl)quinazolin-4-yl)amino)methyl)oxetan-3-yl)carbamate

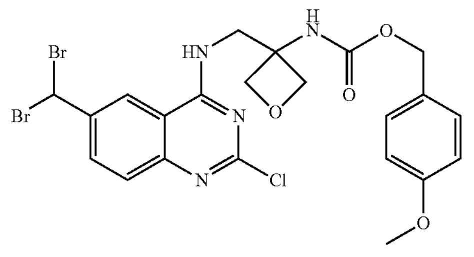

To a solution of 2,4-dichloro-6-(dibromomethyl)quinazoline (5.8 g, 15.6 mmol) in anhydrous tetrahydrofuran (150 mL) was added [3-(aminemethyl)-oxetane-3-yl] carbamic acid p-methoxybenzyl p-chlorobenzoate (7.2 g, 17.2 mmol) and triethylamine (3.9 g, 39.0 mmol). The mixture was stirred at room temperature for 16 hours. The mixture was diluted with ethyl acetate (200 mL), then washed with water (150 mL) and saturated brine (100 mL), then dried over anhydrous sodium sulfate and filtered. The filtrate was concentrated under reduced pressure to obtain a crude product. The crude product was purified by flash column chromatography to give 4-methoxybenzyl (3-(((2-chloro-6-(dibromomethyl)quinazolin-4-yl)amino)methyl)oxetan-3-yl)carbamate (8.2 g) as a yellow solid.

Step 7c

4-Methoxybenzyl (3-(((2-chloro-6-formylquinazolin-4-yl)amino)methyl)oxetan-3-yl)carbamate

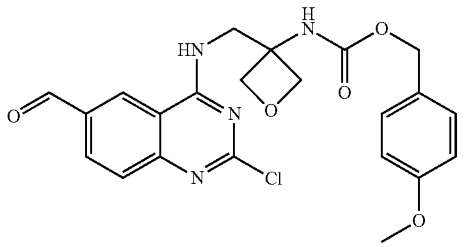 [SMILES: COc1ccc(COC(=O)NC2(CNc3nc(Cl)nc4ccc(C=O)cc34)COC2)cc1]

4-Methoxybenzyl (3-(((2-chloro-6-(dibromomethyl)quinazolin-4-yl)amino)methyl)-oxetan-3-yl)carbamate (4 g, 6.66 mmol) was dissolved in acetonitrile and water (50 mL, v:v=4:1), silver nitrate (2.83 g, 16.6 mmol) was added. The mixture was stirred at room temperature for 2 hours. TLC showed the reaction was completed. The reaction was filtered. The filter cake was washed with ethyl acetate several times, and the filtrate was combined. The filtrate was washed with saturated brine and concentrated to obtain a crude product. The crude product was purified by flash column chromatography to give 4-methoxybenzyl (3-(((2-chloro-6-formylquinazolin-4-yl)amino)methyl)oxetan-3-yl)carbamate (1.2 g) as a white solid.

Step 7d

4-Methoxybenzyl (3-(((2-chloro-6-(difluoromethyl)quinazolin-4-yl)amino)methyl)oxetan-3-yl)carbamate

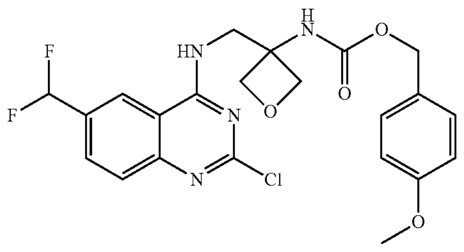 [SMILES: COc1ccc(COC(=O)NC2(CNc3nc(Cl)nc4ccc(C(F)F)cc34)COC2)cc1]

4-Methoxybenzyl (3-(((2-chloro-6-formylquinazolin-4-yl)amino)methyl)oxetan-3-yl)carbamate (570 mg, 1.25 mmol) was dissolved in anhydrous dichloromethane (5 mL) at 0° C., DAST (1.01 g, 6.24 mmol) was added, and the mixture was stirred at room temperature for 4 hours. TLC showed the reaction was completed. The reaction was poured the reaction solution into ice-saturated $NaHCO_3$ solution, and then extracted with dichloromethane three times. The combined organic phases were washed with saturated brine, concentrated to obtain a crude product. The crude product was purified by flash column chromatography to give 4-methoxybenzyl (3-(((2-chloro-6-(difluoromethyl)quinazolin-4-yl)amino)methyl)oxetan-3-yl)carbamate (60 mg) as a white solid.

Step 7e

4-Methoxybenzyl (3-(((6-(difluoromethyl)-2-(1,1-dioxido-2,3-dihydrobenzo[f][1,4]thiazepin-4(5H)-yl)quinazolin-4-yl)amino)methyl)oxetan-3-yl)carbamate

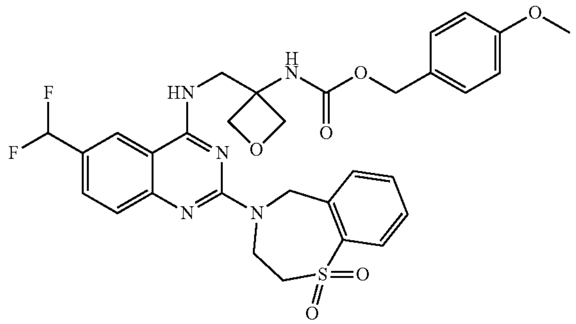 [SMILES: COc1ccc(COC(=O)NC2(CNc3nc(N4CCS(=O)(=O)c5ccccc5C4)nc4ccc(C(F)F)cc34)COC2)cc1]

To a solution of 4-methoxybenzyl (3-(((2-chloro-6-(difluoromethyl)quinazolin-4-yl)amino)methyl)oxetan-3-yl)carbamate (60 mg, 0.12 mmol) in ethanol (5 mL), 2,3,4,5-tetrahydrobenzo[1,4]thiazepine 1,1-dioxide (26 mg, 0.13 mmol) and ammonium chloride (3 mg, 0.06 mmol) were added. The mixture was heated to 80° C. and stirred for 8 hours. The mixture was concentrated to give a crude product. The crude product was dissolved in water (20 mL), then extracted with ethyl acetate (20 mL×3). The combined organic phases were concentrated to obtain the crude product. The crude product was purified by flash column chromatography to give 4-Methoxybenzyl (3-(((6-(difluoromethyl)-2-(1,1-dioxido-2,3-dihydrobenzo[f][1,4]thiazepin-4(5H)-yl)quinazolin-4-yl)amino)methyl)oxetan-3-yl)carbamate (50 mg) as a white solid.

Step 7f 4-(4-(((3-Aminooxetan-3-yl)methyl)amino)-6-(difluoromethyl)quinazolin-2-yl)-2,3,4,5-tetrahydrobenzo[f][1,4]thiazepine 1,1-dioxide

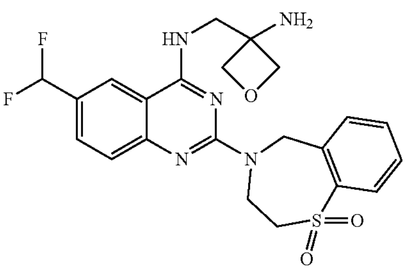 [SMILES: NC1(CNc2nc(N3CCS(=O)(=O)c4ccccc4C3)nc3ccc(C(F)F)cc23)COC1]

4-Methoxybenzyl (3-(((6-(difluoromethyl)-2-(1,1-dioxido-2,3-dihydrobenzo[f][1,4]-thiazepin-4(5H)-yl)quinazolin-4-yl)amino)methyl)oxetan-3-yl)carbamate (50 mg, 0.078 mmol) was subjected to a reaction in a similar manner according to the preparing method depicted in Step 1h of Example 1, to give 4-(4-(((3-aminooxetan-3-yl)methyl)amino)-6-(difluoromethyl)quinazolin-2-yl)-2,3,4,5-tetrahydrobenzo[f][1,4]thiazepine 1,1-dioxide (23.6 mg) as a white solid.

$^1$HNMR (400 MHz, $CD_3OD$) δ 8.14 (s, 1H), 7.98 (d, J=8.0 Hz, 1H), 7.90 (d, J=8.0 Hz, 1H), 7.70 (d, J=8.0 Hz, 1H), 7.61 (t, J=8.0 Hz, 1H), 7.52 (d, J=8.0 Hz, 1H), 7.45 (t, J=8.0 Hz, 1H), 6.79 (t, J=56.0 Hz, 1H), 5.25 (br. s, 2H), 4.82-4.69 (m, 6H), 4.27 (s, 2H), 3.53 (s, 2H).

MS (ESI$^+$) [(M+H)$^+$]: 476.

Example 8

4-(4-(((3-Hydroxyazetidin-3-yl)methyl)amino)-6-methylquinazolin-2-yl)-2,3,4,5-tetrahydrobenzo[f][1,4]thiazepine 1,1-dioxide

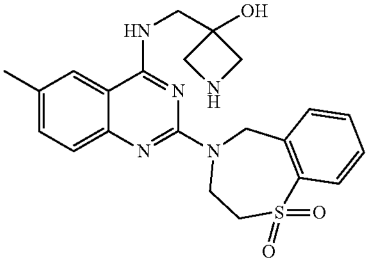 [SMILES: Cc1ccc2nc(N3CCS(=O)(=O)c4ccccc4C3)nc(NCC3(O)CNC3)c2c1]

Step 8a

Tert-butyl 3-(((2-(1,1-dioxido-2,3-dihydrobenzo[f][1,4]thiazepin-4(5H)-yl)-6-methylquinazolin-4-yl)amino)methyl)-3-hydroxyazetidine-1-carboxylate

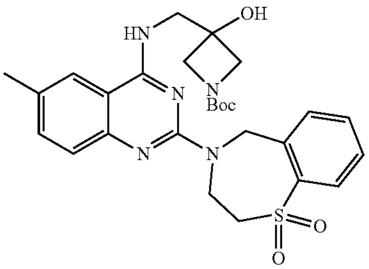 [SMILES: Cc1ccc2nc(N3CCS(=O)(=O)c4ccccc4C3)nc(NCC3(O)CN(C(=O)OC(C)(C)C)C3)c2c1]

4-(4-Chloro-6-methylquinazolin-2-yl)-2,3,4,5-tetrahydrobenzo[f][1,4]thiazepine 1,1-dioxide (100 mg, 0.27 mmol) reacted with tert-butyl 3-(aminomethyl)-3-hydroxyazetidine-1-carboxylate (162 mg, 0.80 mmol) in a similar manner according to the preparing method depicted in Step 1d of Example 1, to give tert-butyl 3-(((2-(1,1-dioxido-2,3-dihydrobenzo[f][1,4]thiazepin-4(5H)-yl)-6-methylquinazolin-4-yl)amino)methyl)-3-hydroxyazetidine-1-carboxylate (135 mg) as a white solid.

MS (ESI$^+$)[(M+H)$^+$]: 540.

Step 8b 4-(4-(((3-Hydroxyazetidin-3-yl)methyl)amino)-6-methylquinazolin-2-yl)-2,3,4,5-tetrahydrobenzo[f][1,4]thiazepine 1,1-dioxide

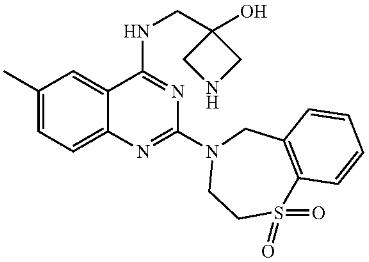 [SMILES: Cc1ccc2nc(N3CCS(=O)(=O)c4ccccc4C3)nc(NCC3(O)CNC3)c2c1]

Tert-butyl 3-(((2-(1,1-dioxido-2,3-dihydrobenzo[f][1,4]thiazepin-4(5H)-yl)-6-methyl-quinazolin-4-yl)amino)methyl)-3-hydroxyazetidine-1-carboxylate (80 mg, 0.15 mmol) was subjected to a reaction in a similar manner according to the preparing method depicted in Step 1e of Example 1, to give 4-(4-(((3-Hydroxyazetidin-3-yl)methyl)amino)-6-methylquinazolin-2-yl)-2,3,4,5-tetrahydrobenzo[f][1,4]thiazepine 1,1-dioxide (21.9 mg) as a white solid.

$^1$H NMR (400 MHz, $CD_3OD$) δ 7.95 (d, J=8.0 Hz, 1H), 7.83 (d, J=7.6 Hz, 1H), 7.70 (s, 1H), 7.58 (td, J=7.6, 1.2 Hz, 1H), 7.44-7.39 (m, 2H), 7.35 (d, J=8.8 Hz, 1H), 5.16 (br. s, 2H), 4.54 (br. s, 2H), 4.28 (d, J=12.4 Hz, 2H), 3.98-3.87 (m, 4H), 3.94 (t, J=5.2 Hz, 2H), 2.39 (s, 3H).

MS (ESI$^+$)[(M+H)$^+$]: 440.

Example 9

4-(4-(3-(Aminomethyl)-3-hydroxypyrrolidin-1-yl)-6-methylquinazolin-2-yl)-2,3,4,5-tetrahydrobenzo[f][1,4]thiazepine 1,1-dioxide

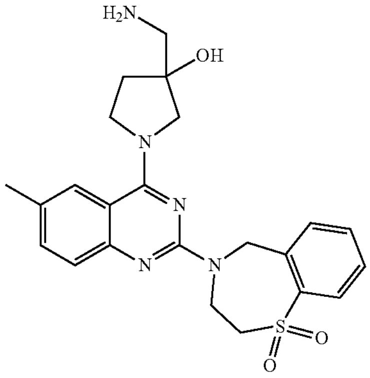 [SMILES: Cc1ccc2nc(N3CCS(=O)(=O)c4ccccc4C3)nc(N3CCC(O)(CN)C3)c2c1]

Step 9a

Tert-butyl ((1-(2-(1,1-dioxido-2,3-dihydrobenzo[f][1,4]thiazepin-4(5H)-yl)-6-methylquinazolin-4-yl)-3-hydroxypyrrolidin-3-yl)methyl)carbamate

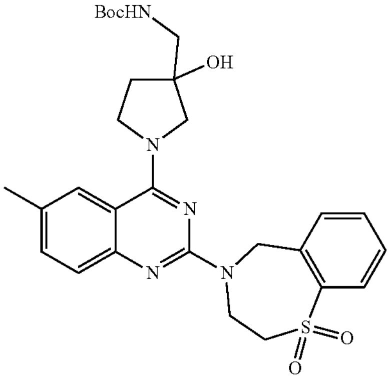 [SMILES: Cc1ccc2nc(N3CCS(=O)(=O)c4ccccc4C3)nc(N3CCC(O)(CNC(=O)OC(C)(C)C)C3)c2c1]

4-(4-Chloro-6-methylquinazolin-2-yl)-2,3,4,5-tetrahydrobenzo[f][1,4]thiazepine 1,1-dioxide (500 mg, 1.41 mmol) and tert-butyl ((3-hydroxypyrrol-3-yl)methyl)carbamate (338 mg, 1.69 mmol) were dissolved in 5 mL DMF in a nitrogen atmosphere, PyBOP and DBU were added, and then heated to 60° C. and stirred for 3-4 hours. The reaction was diluted with water and extracted with ethyl acetate (10 mL×3). The combined organic phases were washed with saturated brine (15 mL×3), dried over anhydrous sodium sulfate and filtered. The filtrate was concentrated at reduced pressure to obtain a crude product. The crude product was purified by flash column chromatography to give tert-butyl ((1-(2-(1,1-dioxido-2,3-dihydrobenzo[f][1,4]thiazepin-4(5H)-yl)-6-methylquinazolin-4-yl)-3-hydroxypyrrolidin-3-yl)methyl)carbamate (127 mg) as a yellow solid.

Step 9b

4-(4-(3-(Aminomethyl)-3-hydroxypyrrolidin-1-yl)-6-methylquinazolin-2-yl)-2,3,4,5-tetrahydrobenzo[f][1,4]thiazepine 1,1-dioxide

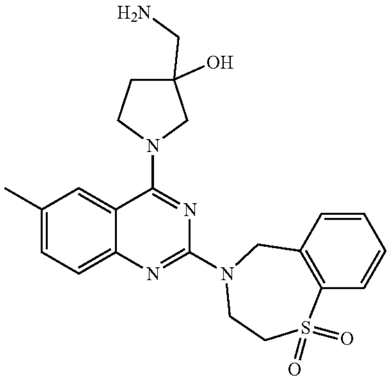 [SMILES: Cc1ccc2nc(N3CCS(=O)(=O)c4ccccc4C3)nc(N3CCC(O)(CN)C3)c2c1]

Tert-butyl ((1-(2-(1,1-dioxido-2,3-dihydrobenzo[f][1,4]thiazepin-4(5H)-yl)-6-methyl-quinazolin-4-yl)-3-hydroxy-pyrrolidin-3-yl)methyl)carbamate (127 mg, 0.24 mmol) was subjected to a reaction in a similar manner according to the preparing method depicted in Step 1e of Example 1, to give 4-(4-(3-(aminomethyl)-3-hydroxypyrrolidin-1-yl)-6-methylquinazolin-2-yl)-2,3,4,5-tetrahydrobenzo[f][1,4]thiazepine 1,1-dioxide (24.2 mg) as white powder.

$^1$H NMR (400 MHz, $CD_3OD$) δ 7.95 (d, J=8.0 Hz, 1H), 7.83-7.76 (m, 2H), 7.58 (t, J=7.8 Hz, 1H), 7.45-7.41 (m, 1H), 7.34 (s, 2H), 5.17 (br. S, 2H), 4.54 (br. S, 2H), 4.25-4.19 (m, 1H), 4.05-3.92 (m, 2H), 3.85-3.80 (m, 1H), 3.55-3.48 (m, 2H), 2.91 (s, 2H), 2.37 (s, 3H), 2.07-2.02 (m, 2H).

MS (ESI$^+$) [(M+H)$^+$]: 453.

Example 10

4-(4-(3-(Aminomethyl)-3-hydroxyazetidin-1-yl)-6-methylquinazolin-2-yl)-2,3,4,5-tetrahydrobenzo[f][1,4]thiazepine 1,1-dioxide

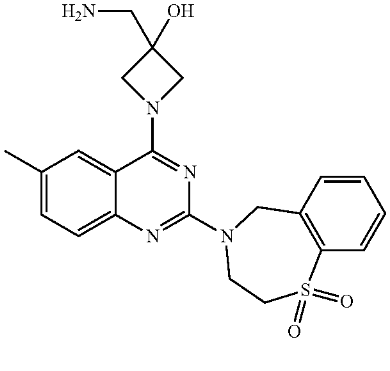 [SMILES: Cc1ccc2nc(N3CCS(=O)(=O)c4ccccc4C3)nc(N3CC(O)(CN)C3)c2c1]

Step 10a

Tert-butyl ((1-(2-(1,1-dioxido-2,3-dihydrobenzo[f][1,4]thiazepine-4(5H)-yl)-6-methylquinazolin-4-yl)-3-hydroxyazetidin-3-yl)methyl)carbamate

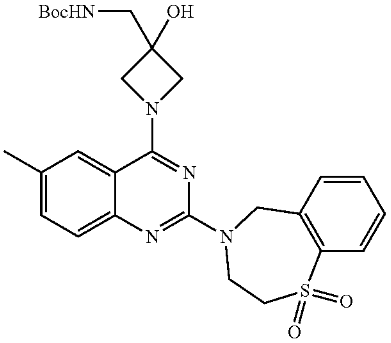 [SMILES: Cc1ccc2nc(N3CCS(=O)(=O)c4ccccc4C3)nc(N3CC(O)(CNC(=O)OC(C)(C)C)C3)c2c1]

4-(4-Chloro-6-methylquinazolin-2-yl)-2,3,4,5-tetrahydrobenzo[f][1,4]thiazepine 1,1-dioxide (444 mg, 1.19 mmol) reacted with tert-butyl ((3-hydroxyazetidin-3-yl)methyl)carbamate (150 mg, 0.74 mmol) in a similar manner according to the preparing method depicted in Step 1d of Example 1, to give tert-butyl ((1-(2-(1,1-dioxido-2,3-dihydrobenzo[f][1,4]thiazepine-4(5H)-yl)-6-methylquinazolin-4-yl)-3-hydroxyazetidin-3-yl)methyl)carbamate (320 mg) as a white solid.

Step 10b 4-(4-(3-(Aminomethyl)-3-hydroxyazetidin-1-yl)-6-methylquinazolin-2-yl)-2,3,4,5-tetrahydrobenzo[f][1,4]thiazepine 1,1-dioxide

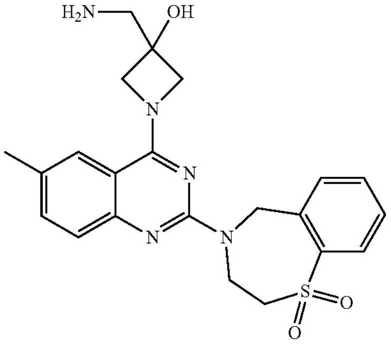 [SMILES: Cc1ccc2nc(N3CCS(=O)(=O)c4ccccc4C3)nc(N3CC(O)(CN)C3)c2c1]

Tert-butyl ((1-(2-(1,1-dioxido-2,3-dihydrobenzo[f][1,4]thiazepine-4(5H)-yl)-6-methylquinazolin-4-yl)-3-hydroxyazetidin-3-yl)methyl)carbamate (80 mg, 0.15 mmol) was subjected to a reaction in a similar manner according to the preparing method depicted in Step 1e of Example 1, to give 4-(4-(3-(aminomethyl)-3-hydroxyazetidin-1-yl)-6-methylquinazolin-2-yl)-2,3,4,5-tetrahydrobenzo[f][1,4]thiazepine 1,1-dioxide (21.9 mg) as white powder.

$^1$H NMR (400 MHz, $CD_3OD$) δ 7.96 (d, J=7.6 Hz, 1H), 7.79 (d, J=7.2 Hz, 1H), 7.60 (t, J=8.0 Hz, 1H), 7.49 (s, 1H), 7.45 (d, J=7.6 Hz, 1H), 7.41 (dd, J=8.0, 1.6 Hz, 1H), 7.37 (d, J=8.4 Hz, 1H), 5.18 (s, 2H), 4.63 (d, J=9.6 Hz, 2H), 4.55 (s, 2H), 4.42 (d, J=10.0 Hz, 2H), 3.51 (t, J=5.0 Hz, 2H), 3.37 (s, 2H), 2.36 (s, 3H).

MS $(ESI^+)[(M+H)^+]$: 440.

Example 11

4-(4-(3-(Aminomethyl)azetidin-1-yl)-6-methylquinazolin-2-yl)-2,3,4,5-tetrahydrobenzo[f][1,4]thiazepine 1,1-dioxide

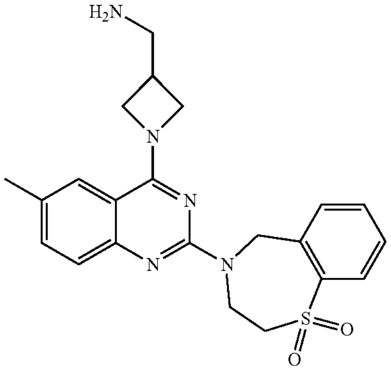 [SMILES: Cc1ccc2nc(N3CCS(=O)(=O)c4ccccc4C3)nc(N3CC(CN)C3)c2c1]

Step 11a

Tert-butyl ((1-(2-(1,1-dioxido-2,3-dihydrobenzo[f][1,4]thiazepin-4(5H)-yl)-6-methylquinazolin-4-yl)azetidin-3-yl)methyl)carbamate

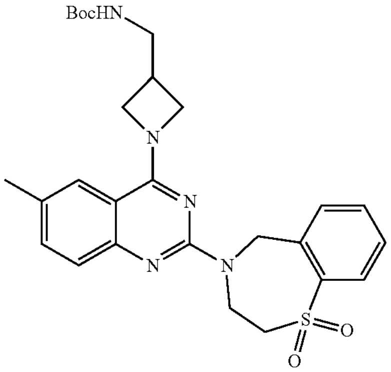 [SMILES: Cc1ccc2nc(N3CCS(=O)(=O)c4ccccc4C3)nc(N3CC(CNC(=O)OC(C)(C)C)C3)c2c1]

4-(4-Chloro-6-methylquinazolin-2-yl)-2,3,4,5-tetrahydrobenzo[f][1,4]thiazepine 1,1-dioxide (80 mg, 0.21 mmol) reacted with tert-butyl (azetidin-3-ylmethyl)carbamate (48 mg, 0.26 mmol) in a similar manner according to the preparing method depicted in Step 1d of Example 1, to give tert-butyl ((1-(2-(1,1-dioxido-2,3-dihydrobenzo[f][1,4]thiazepin-4(5H)-yl)-6-methylquinazolin-4-yl)azetidin-3-yl)methyl)carbamate (66 mg) as a white solid.

Step 11b 4-(4-(3-(Aminomethyl)azetidin-1-yl)-6-methylquinazolin-2-yl)-2,3,4,5-tetrahydrobenzo[f][1,4]thiazepine 1,1-dioxide

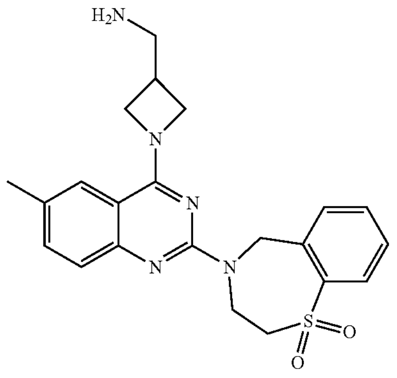 [SMILES: Cc1ccc2nc(N3CCS(=O)(=O)c4ccccc4C3)nc(N3CC(CN)C3)c2c1]

Tert-butyl ((1-(2-(1,1-dioxido-2,3-dihydrobenzo[f][1,4]thiazepin-4(5H)-yl)-6-methyl-quinazolin-4-yl)thiazepin-3-yl)methyl)carbamate (66 mg, 0.13 mmol) was subjected to a reaction in a similar manner according to the preparing method depicted in Step 1e of Example 1, to give 4-(4-(3-(Aminomethyl)thiazepin-1-yl)-6-methylquinazolin-2-yl)-2,3,4,5-tetrahydrobenzo[f][1,4]thiazepine 1,1-dioxide (18.3 mg) as white powder.

$^1$H NMR (400 MHz, $CD_3OD$) δ 7.95 (d, J=8.0 Hz, 1H), 7.79 (d, J=8.0 Hz, 1H), 7.60-7.56 (m, 1H), 7.50 (s, 1H), 7.44-7.40 (m, 1H), 7.36-7.30 (m, 2H), 5.15 (br. S, 2H), 4.61-4.38 (m, 4H), 4.23-4.20 (m, 2H), 3.32-3.30 (m, 2H), 2.98 (d, J=9.6 Hz, 2H), 2.91-2.84 (m, 1H), 2.34 (s, 3H).

MS ($ESI^+$)[$(M+H)^+$]: 424.

Example 12

4-(4-((3-Aminocyclobutyl)amino)-6-methylquinazolin-2-yl)-2,3,4,5-tetrahydrobenzo[f][1,4]thiazepine 1,1-dioxide

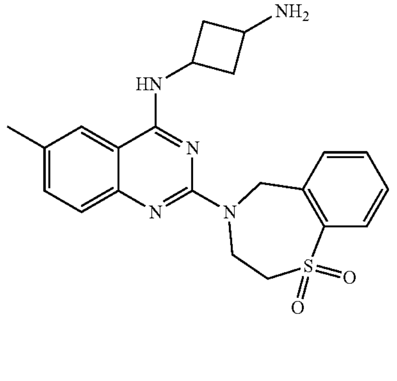 [SMILES: Cc1ccc2nc(N3CCS(=O)(=O)c4ccccc4C3)nc(NC3CC(N)C3)c2c1]

Step 12a

Tert-butyl (3-((2-(1,1-dioxido-2,3-dihydrobenzo[f][1,4]thiazepine-4(5H)-yl)-6-methylquinazolin-4-yl)amino)cyclobutyl)carbamate

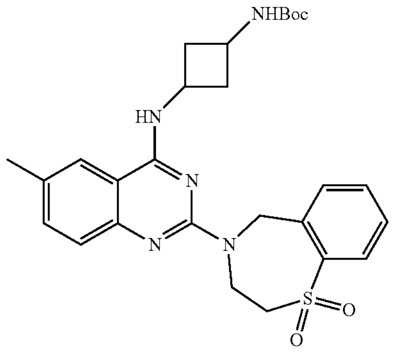 [SMILES: Cc1ccc2nc(N3CCS(=O)(=O)c4ccccc4C3)nc(NC3CC(NC(=O)OC(C)(C)C)C3)c2c1]

4-(4-Chloro-6-methylquinazolin-2-yl)-2,3,4,5-tetrahydrobenzo[f][1,4]thiazepine 1,1-dioxide (180 mg, 0.48 mmol) reacted with tert-butyl (3-aminocyclobutyl)carbamate (98 mg, 0.53 mmol) in a similar manner according to the preparing method depicted in Step 1d of Example 1, to give tert-butyl (3-((2-(1,1-dioxido-2,3-dihydrobenzo[f][1,4]thiazepine-4(5H)-yl)-6-methylquinazolin-4-yl)amino)cyclobutyl)carbamate (105 mg) as a white solid.

Step 12b 4-(4-((3-Aminocyclobutyl)amino)-6-methylquinazolin-2-yl)-2,3,4,5-tetrahydrobenzo[f][1,4]thiazepine 1,1-dioxide

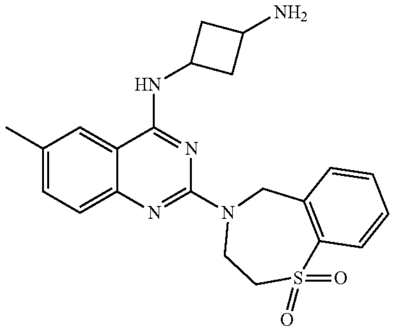 [SMILES: Cc1ccc2nc(N3CCS(=O)(=O)c4ccccc4C3)nc(NC3CC(N)C3)c2c1]

Tert-butyl (3-((2-(1,1-dioxido-2,3-dihydrobenzo[f][1,4]thiazepine-4(5H)-yl)-6-methyl-quinazolin-4-yl)amino)cyclobutyl)carbamate (105 mg, 0.20 mmol) was subjected to a reaction in a similar manner according to the preparing method depicted in Step 1e of Example 1, to give 4-(4-((3-Aminocyclobutyl)amino)-6-methylquinazolin-2-yl)-2,3,4,5-tetrahydro-benzo[f][1,4]thiazepine 1,1-dioxide (40.4 mg) as white powder.

$^1$H NMR (400 MHz, $CD_3OD$) δ 7.95 (d, J=8.0 Hz, 1H), 7.85-7.79 (m, 1H), 7.72-7.66 (m, 1H), 7.60-7.55 (m, 1H), 7.43-7.39 (m, 1H), 7.37-7.34 (m, 1H), 7.30-7.28 (m, 1H), 5.17 (br. s, 2H), 4.54-4.41 (m, 3H), 3.77-3.71 (m, 1H), 3.49 (t, J=8.0 Hz, 2H), 2.88-2.82 (m, 1H), 2.51-2.44 (m, 2H), 2.37 (s, 3H) 1.93-1.85 (m, 1H).

MS ($ESI^+$)[$(M+H)^+$]: 424.

Example 13

4-(4-(3-Amino-3-(aminomethyl)azetidin-1-yl)-6-methylquinazolin-2-yl)-2,3,4,5-tetrahydrobenzo[f][1,4]thiazepine 1,1-dioxide

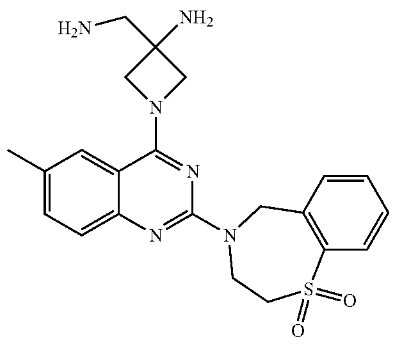 [SMILES: Cc1ccc2nc(N3CCS(=O)(=O)c4ccccc4C3)nc(N3CC(N)(CN)C3)c2c1]

Step 13a

Tert-butyl 3-(bis(4-methoxybenzyl)amino)-3-cyano-azetidine-1-carboxylate

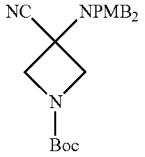

Tert-butyl 3-oxoazetidine-1-carboxylate (1.00 g, 5.84 mmol) and bis(4-methoxybenzyl)amine (3.76 g, 14.6 mmol) were dissolved in glacial acetic acid (20 mL) at room temperature, trimethylsilyl nitrile (724 mg, 7.30 mmol) was added. The reaction solution was heated to 80° C. and reacted for 4 hours. After cooling, it was concentrated to remove acetic acid. The residue was dissolved in ethyl acetate (10 mL), washed with saturated sodium bicarbonate solution (10 mL×3), then washed with saturated brine (10 mL), dried over anhydrous sodium sulfate and filtered. The filtrate was concentrated under reduced pressure to obtain a crude product. The crude product was purified by flash column chromatography to give tert-butyl 3-(bis(4-methoxybenzyl)amino)-3-cyanoazetidine-1-carboxylate (1.75 g) as a colorless oil.

Step 13b 3-(Bis(4-methoxybenzyl)amino)azetidine-3-carbonitrile

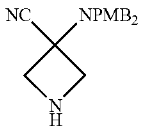

To a solution of tert-butyl 3-(bis(4-methoxybenzyl)amino)-3-cyanoazetidine-1-carboxylate (910 mg, 2.08 mmol) in dichloromethane (3 mL) at room temperature, trifluoroacetic acid (1 mL) was added. The mixture was stirred at room temperature for 1 hour, then the reaction mixture was concentrated under reduced pressure, diluted with ethyl acetate (20 mL), and washed with saturated sodium bicarbonate solution (10 mL). The aqueous phase was extracted with 10% methanol in dichloromethane solution (15 mL×2), then the combined organic phases were washed with saturated brine (10 mL), dried over anhydrous sodium sulfate and filtered. The filtrate was concentrated under reduced pressure to obtain a crude product. The crude product was purified by flash column chromatography to give 3-(bis(4-methoxybenzyl)amino)azetidine-3-carbonitrile (267 mg) as a colorless oil.

Step 13c 3-(Bis(4-methoxybenzyl)amino)-1-(2-(1,1-dioxido-2,3-dihydrobenzo[f][1,4]thiazepin-4(5H)-yl)-6-methylquinazolin-4-yl)azetidine-3-carbonitrile

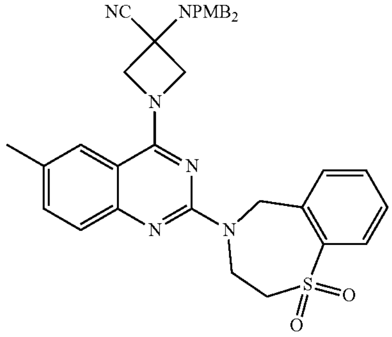

4-(4-Chloro-6-methylquinazolin-2-yl)-2,3,4,5-tetrahydrobenzo[f][1,4]thiazepine-1,1-dioxide (296 mg, 0.79 mmol) reacted with 3-(bis(4-methoxybenzyl)amino)azetidine-3-carbonitrile (267 mg, 0.79 mmol) in a similar manner according to the preparing method depicted in Step 1d of Example 1, to give 3-(bis(4-methoxybenzyl)amino)-1-(2-(1,1-dioxido-2,3-dihydrobenzo[f][1,4]thiazepin-4(5H)-yl)-6-methylquinazolin-4-yl)azetidine-3-carbonitrile (340 mg) as a white solid.

Step 13d

3-Amino-1-(2-(1,1-dioxido-2,3-dihydrobenzo[f][1,4]thiazepin-4(5H)-yl)-6-methylquinazolin-4-yl)azetidine-3-carbonitrile

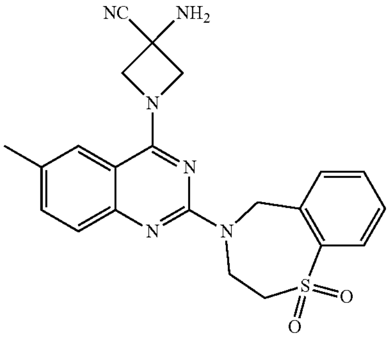 [SMILES: Cc1ccc2nc(N3CCS(=O)(=O)c4ccccc4C3)nc(N3CC(N)(C#N)C3)c2c1]

3-(Bis(4-methoxybenzyl)amino)-1-(2-(1,1-dioxido-2,3-dihydrobenzo[f][1,4]thiazepin-4(5H)-yl)-6-methylquinazolin-4-yl)azetidine-3-carbonitrile (340 mg, 0.50 mmol) was dissolved in trifluoroacetic acid (3 mL). The mixture was stirred at 60° C. for 2 hours, then the reaction mixture was concentrated under reduced pressure, diluted with ethyl acetate (20 mL), and washed with saturated sodium bicarbonate solution (10 mL). The aqueous phase was extracted with 10% methanol in dichloromethane solution (15 mL×2), then the combined organic phases were washed with saturated brine (10 mL), dried over anhydrous sodium sulfate and filtered. The filtrate was concentrated under reduced pressure to obtain a crude product. The crude product was purified by flash column chromatography to give 3-amino-1-(2-(1,1-dioxido-2,3-dihydrobenzo[f][1,4]thiazepin-4(5H)-yl)-6-methylquinazolin-4-yl)azetidine-3-carbonitrile (130 mg) as a white solid.

Step 13e 4-(4-(3-Amino-3-(aminomethyl)azetidin-1-yl)-6-methylquinazolin-2-yl)-2,3,4,5-tetrahydrobenzo[f][1,4]thiazepine 1,1-dioxide

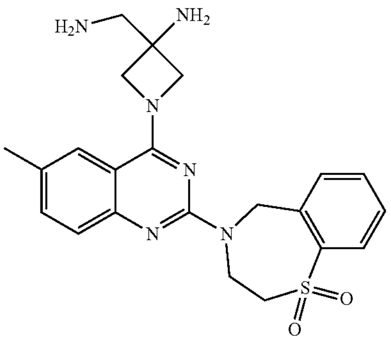 [SMILES: Cc1ccc2nc(N3CCS(=O)(=O)c4ccccc4C3)nc(N3CC(N)(CN)C3)c2c1]

To a solution of 3-amino-1-(2-(1,1-dioxido-2,3-dihydrobenzo[f][1,4]thiazepin-4(5H)-yl)-6-methylquinazolin-4-yl)azetidine-3-carbonitrile (130 mg, 0.30 mmol) in methanol (3 mL) under ice-bath, nickel chloride hexahydrate (233 mg, 0.98 mmol) and sodium borohydride (37 mg, 0.98 mmol) were added. The mixture was stirred for 2 hours at room temperature. Water (10 mL) was added to quench the reaction, then filtered, and the mother liquor was extracted with 10% methanol in dichloromethane (15 mL×2), then the combined organic phases were washed with saturated brine (10 mL), and dried over anhydrous sodium sulfate and filtered. The filtrate was concentrated under reduced pressure to obtain a crude product. The crude product was purified by flash column chromatography to give 4-(4-(3-amino-3-(aminomethyl)azetidin-1-yl)-6-methylquinazolin-2-yl)-2,3,4,5-tetrahydrobenzo[f][1,4]thiazepine 1,1-dioxide (16.2 mg) as a white solid.

$^1$H NMR (400 MHz, $CD_3OD$) δ 7.94 (d, J=7.6 Hz, 1H), 7.79 (d, J=7.6 Hz, 1H), 7.58 (t, J=7.2 Hz, 1H), 7.50 (s, 1H), 7.41 (t, J=8.0 Hz, 1H), 7.37 (dd, J=8.0, 1.4 Hz, 1H), 7.33 (d, J=8.4 Hz, 1H), 5.16 (br. s, 2H), 4.55 (br. s, 2H), 4.47 (d, J=9.6 Hz, 2H), 4.23 (d, J=9.2 Hz, 2H), 3.49 (t, J=4.8 Hz, 2H), 3.10 (s, 2H), 2.35 (s, 3H).

MS ($ESI^+$)[$(M+H)^+$]: 439.

Example 14

4-(4-(((3S,4S)-4-hydroxypyrrolidin-3-yl)amino)-6-methylquinazolin-2-yl)-2,3,4,5-tetrahydrobenzo[f][1,4]thiazepine 1,1-dioxide

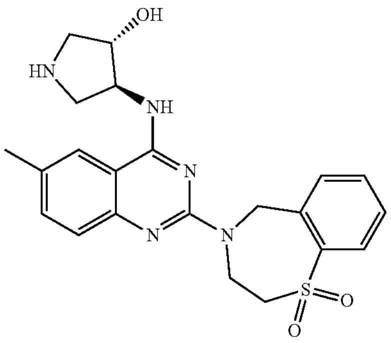 [SMILES: Cc1ccc2nc(N3CCS(=O)(=O)c4ccccc4C3)nc(N[C@H]3CNC[C@@H]3O)c2c1]

Step 14a

Tert-butyl (3S,4S)-3-((2-(1,1-dioxido-2,3-dihydrobenzo[f][1,4]thiazepin-4(5H)-yl)-6-methylquinazolin-4-yl)amino)-4-hydroxypyrrolidine-1-carboxylate

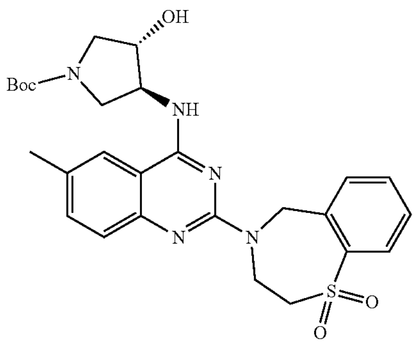 [SMILES: Cc1ccc2nc(N3CCS(=O)(=O)c4ccccc4C3)nc(N[C@H]3CN(C(=O)OC(C)(C)C)C[C@@H]3O)c2c1]

4-(4-Chloro-6-methylquinazolin-2-yl)-2,3,4,5-tetrahydrobenzo[f][1,4]thiazepine 1,1-dioxide and (3S,4S)-tert-butyl 3-amino-4-hydroxypyrrolidine-1-carboxylate (50 mg, 0.25 mmol) were prepared in a similar manner according to the preparing method depicted in Step 1d of Example 1, to give tert-butyl (3S,4S)-3-((2-(1,1-dioxido-2,3-dihydrobenzo[f][1,4]thiazepin-4(5H)-yl)-6-methylquinazolin-4-yl)amino)-4-hydroxypyrrolidine-1-carboxylate (118 mg) as a white solid.

Step 14b 4-(4-(((3S,4S)-4-hydroxypyrrolidin-3-yl)amino)-6-methylquinazolin-2-yl)-2,3,4,5-tetrahydrobenzo[f][1,4]thiazepine 1,1-dioxide

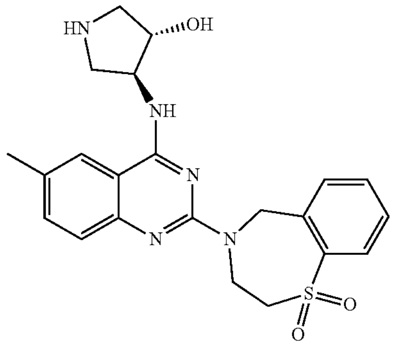 [SMILES: Cc1ccc2nc(N3CCS(=O)(=O)c4ccccc4C3)nc(N[C@H]3CNC[C@@H]3O)c2c1]

Tert-butyl (3S,4S)-3-((2-(1,1-dioxido-2,3-dihydrobenzo[f][1,4]thiazepin-4(5H)-yl)-6-methylquinazolin-4-yl)amino)-4-hydroxypyrrolidine-1-carboxylate (118 mg, 0.22 mmol) was subjected to a reaction in a similar manner according to the preparing method depicted in Step 1e of Example 1, to give 4-(4-(((3S,4S)-4-hydroxypyrrolidin-3-yl)amino)-6-methyl-quinazolin-2-yl)-2,3,4,5-tetrahydrobenzo[f][1,4]thiazepine 1,1-dioxide (62.6 mg) as a white solid.

$^1$H NMR (400 MHz, $CD_3OD$) δ 7.91 (d, J=7.6 Hz, 1H), 7.89 (d, J=7.2 Hz, 1H), 7.75 (s, 1H), 7.57 (t, J=7.2 Hz, 1H), 7.42-7.34 (m, 2H), 7.31 (d, J=8.0 Hz, 1H), 5.17 (br. s, 2H), 4.72 (br. s, 2H), 4.52 (br. s, 2H), 3.78 (dd, J=12.4, 5.6 Hz, 1H), 3.54-3.43 (m, 3H), 3.39 (d, J=12.0 Hz, 1H), 3.23 (d, J=12.0 Hz, 1H), 2.36 (s, 3H).

MS $(ESI^+)[(M+H)^+]$: 440.

Example 15

4-(4-((2-azaspiro[3.3]heptan-6-yl)amino)-6-methylquinazolin-2-yl)-2,3,4,5-tetrahydrobenzo[f][1,4]thiazepine 1,1-dioxide

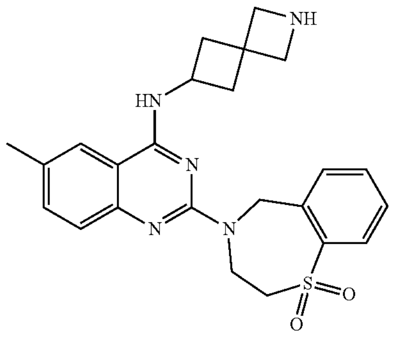 [SMILES: Cc1ccc2nc(N3CCS(=O)(=O)c4ccccc4C3)nc(NC3CC4(CNC4)C3)c2c1]

Step 15a

Tert-butyl 6-((2-(1,1-dioxido-2,3-dihydrobenzo[f][1,4]thiazepin-4(5H)-yl)-6-methylquinazolin-4-yl)amino)-2-azaspiro[3.3]heptane-2-carboxylate

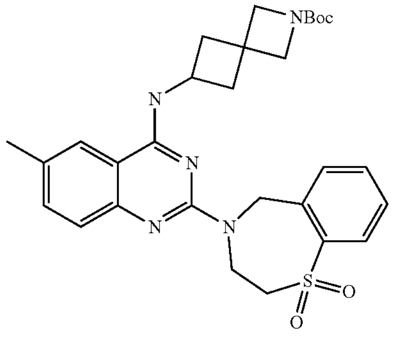 [SMILES: Cc1ccc2nc(N3CCS(=O)(=O)c4ccccc4C3)nc(NC3CC4(C3)CN(C(=O)OC(C)(C)C)C4)c2c1]

4-(4-Chloro-6-methylquinazolin-2-yl)-2,3,4,5-tetrahydrobenzo[f][1,4]thiazepine-1,1-dioxide (120 mg, 0.32 mmol) reacted with tert-butyl 6-amino-2-azaspiro[3.3]heptane-2-carboxylate (68 mg, 0.32 mmol) in a similar manner according to the preparing method depicted in Step 1d of Example 1, to give tert-butyl 6-((2-(1,1-dioxido-2,3-dihydrobenzo[f][1,4]thiazepin-4(5H)-yl)-6-methylquinazolin-4-yl)amino)-2-azaspiro[3.3]heptane-2-carboxylate (150 mg) as a white solid.

Step 15b 4-(4-((2-Azaspiro[3.3]heptan-6-yl)amino)-6-methylquinazolin-2-yl)-2,3,4,5-tetrahydrobenzo[f][1,4]thiazepine 1,1-dioxide

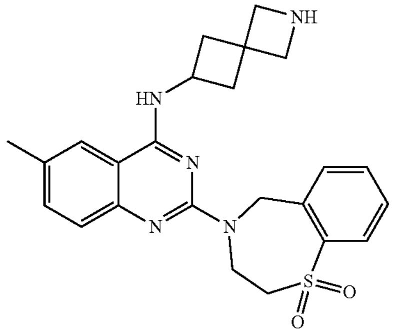 [SMILES: Cc1ccc2nc(N3CCS(=O)(=O)c4ccccc4C3)nc(NC3CC4(CNC4)C3)c2c1]

Tert-butyl 6-((2-(1,1-dioxido-2,3-dihydrobenzo[f][1,4]thiazepin-4(5H)-yl)-6-methyl-quinazolin-4-yl)amino)-2-azaspiro[3.3]heptane-2-carboxylate (150 mg, 0.27 mmol) was subjected to a reaction in a similar manner according to the preparing method depicted in Step 1e of Example 1, to give 4-(4-((2-azaspiro[3.3]heptan-6-yl)amino)-6-methylquinazolin-2-yl)-2,3,4,5-tetrahydrobenzo[f][1,4]thiazepine 1,1-dioxide (108.5 mg) as a white solid.

$^1$H NMR (400 MHz, $CD_3OD$) δ 7.93 (d, J=7.6 Hz, 1H), 7.76 (d, J=7.2 Hz, 1H), 7.65 (s, 1H), 7.56 (t, J=7.6 Hz, 1H), 7.38 (t, J=7.6 Hz, 1H), 7.33 (d, J=8.8 Hz, 1H), 7.26 (d, J=8.4 Hz, 1H), 5.14 (br. s, 2H), 4.65-4.40 (br. s, 3H), 3.93 (s, 2H), 3.74 (s, 2H), 3.49 (t, J=4.6 Hz, 2H), 2.76 (t, J=9.6 Hz, 2H), 2.35 (s, 3H), 2.29 (t, J=10.0 Hz, 2H).

MS($ESI^+$)[$(M+H)^+$]: 450.

The biological implementation data are specifically described below to further illustrate the technical solution of the present disclosure.

Materials and Methods

RSV Cell Line:

HEp-2 cells (ATCC CCL-23, human laryngeal carcinoma epithelial cells) were purchased from American Type Culture Collection and the culture conditions were as follows: 1% double antibody was added to Dulbecco modified Eagle medium (DMEM) medium containing 10% fetal bovine serum (FBS), and maintained in a 5% $CO_2$ incubator and cultured at 37° C.

Virus Cytopathic Effect (CPE) Assay:

To evaluate the anti-RSV activity of compounds, cells were seeded in a 96-well plate at a density of $5\times10^3$ cells/well in Hyclone™ (DMEM) containing 10% fetal bovine serum (FBS). The following day, cells were infected with a 0.5 MOI of RSV Long strain (ATCC) in the presence of 3-fold serial dilutions of compound to a total volume of 100 μL per well. The cell viability was evaluated by the cell counting kit CellTiter-Glo Reagent after 4 days. The fluorescence signal was read on a multi-mode microplate reader and the 50% effective concentration $EC_{50}$ was determined by the fluorescence value.

Results

The RSV inhibition activities of the compounds involved in Examples 1 to 15 disclosed herein were evaluated according to the above method, and the results are shown in Table 3 below.

TABLE 3

Activity Data for the Examples

| Example No. | $IC_{50}$(nM) | Example No. | $IC_{50}$(nM) |
|---|---|---|---|
| 1 | 4.4 | 2 | 6.3 |
| 3 | 5.0 | 4 | 7.0 |
| 5 | 7.9 | 6 | 4.9 |
| 7 | 4.1 | 8 | 2.9 |
| 9 | 0.9 | 10 | 3.3 |
| 11 | 1.2 | 12 | 1.7 |
| 13 | 9.6 | 14 | 1.3 |
| 15 | 3.7 | | |

The pharmacokinetics were further tested of Example 4 and Example 7 disclosed herein and Example 61-1 (Comparative Example 1) in patent WO2013020993 in ICR mice. A single intravenous injection (dose of 2 mg/kg) and a single oral administration (dose of 10 mg/kg) were taken respectively. Blood collection point: before administration, 5 min, 15 min, 30 min, 1 h, 2 h, 4 h, 8 h, 12 h, 24 h after administration. The pharmacokinetic parameters of Example 4 and Example 7 in mouse plasma are shown in Table 5 below. The same method was applied to the pharmacokinetics of the above Comparative Example 1 in ICR mice, with a single intravenous injection (dose of 2 mg/kg) and a single oral administration (dose of 10 mg/kg) respectively. The pharmacokinetic parameters of Comparative Example 1 in mouse plasma and liver are shown in Table 4 below:

TABLE 4

Plasma drug concentrations in mice

| | Example 4 | | Example 7 | | Comparative Example 1 | |
|---|---|---|---|---|---|---|
| Time (hour) | i.v. (2 mg/kg) Plasma (ng/mL) | p.o. (10 mg/kg) Plasma (ng/mL) | i.v. (2 mg/kg) Plasma (ng/mL) | p.o. (10 mg/kg) Plasma (ng/mL) | i.v. (2 mg/kg) Plasma (ng/mL) | p.o. (10 mg/kg) Plasma (ng/mL) |
| 0.083 | 38.0 | 49.7 | 815.3 | 233.3 | 18.9 | 42.5 |
| 0.25 | 38.4 | 273.7 | 540.3 | 262.3 | 13.4 | 107.0 |
| 0.5 | 30.7 | 406.7 | 334.7 | 286.7 | 7.4 | 74.2 |
| 1 | 34.5 | 432.0 | 128.3 | 179.9 | 5.0 | 41.3 |
| 2 | 43.9 | 505.3 | 35.0 | 50.1 | 5.7 | 10.6 |
| 4 | 82.4 | 379.7 | 12.3 | 16.7 | 4.3 | 4.5 |
| 8 | 62.8 | 127.5 | 2.7 | 4.6 | ND[2] | ND |
| 12 | NA[1] | NA | 1.3 | 2.9 | ND | ND |
| 24 | 1.7 | 5.4 | 1.5 | 1.4 | ND | ND |
| $T_{max}$ (hr) | 4.00 | 2.00 | 0.08 | 0.50 | 0.08 | 0.25 |
| $C_{max}$ (ng/mL) | 82.4 | 505.3 | 815.3 | 286.7 | 18.9 | 107 |
| $AUC_{0-12}$ (ng/mL*hr) | 1006.4 | 3755.0 | 572.6 | 475.7 | 48.7 | 120.6 |
| $AUC_{INF}$ (ng/mL*hr) | 1014.7 | 3781.0 | 579.0 | 481.1 | 75.4 | 130.9 |
| $t_{1/2}$ (hr) | 3.4 | 3.3 | 1.6 | 1.3 | 8.1 | 3.0 |
| CL (mL/hr/kg) | 1970.9 | / | 3454.0 | / | 26531.5 | / |
| Vss (mL/kg) | 13104.9 | / | 3329.1 | / | 295996.7 | / |
| F | 74.6% | | 16.62% | | 49.6% | |

NA: Not Apply;
ND: Not Detected.

As shown in Table 4, the average concentration in mouse plasma after intravenous injection and oral administration of the compounds disclosed herein is significantly higher than that of the Comparative Example 1. The compounds disclosed herein demonstrated a higher exposure in vivo and more effective for the treatment of RSV disease.

Further, those skilled in the art understand that the compound of formula I, the different realization modes of the compound of formula I and all the example compounds of formula I disclosed herein can be prepared into the corresponding isomers, solvates, hydrates, prodrugs, stable isotope derivatives and pharmaceutically acceptable salts thereof. Preferably, the compound is prepared into a pharmaceutically acceptable derivative, wherein the derivative is selected from anyone of prodrugs, salts, esters, amides, salts of esters, salts of amides and metabolites thereof.

Further, pharmaceutically acceptable salts are those conventional non-toxic salts formed by any compound disclosed herein with inorganic acids (such as hydrochloric acid, hydrobromic acid, hydroiodic acid, perchloric acid, sulfuric acid or phosphoric acid, etc.), or with organic acids (such as acetic acid, oxalic acid, maleic acid, Fumaric acid, tartaric acid, benzenesulfonic acid, methanesulfonic acid, salicylic acid, succinic acid, citric acid, lactic acid, propionic acid, benzoic acid, p-toluenesulfonic acid, malic acid, etc.). A review of suitable pharmaceutically acceptable salts refers to: Berge S. M et al., *J. Pharm. Sci.,* 1977, 66, 1-19; Gould P. L., *Int. J. Pharm.,* 1986, 33, 201-277; Marcel Dekker Inc, New York 1996, 13, 453-497.

Further, stable isotope derivatives can introduce isotopes into any compound disclosed herein, and the introduced isotopes can be $^{2}H$, $^{3}H$, $^{13}C$, $^{14}C$, $^{15}N$, $^{17}O$, $^{18}O$, $^{31}P$, $^{32}P$, $^{35}S$, $^{18}F$, $^{36}Cl$, specific isotopic derivatives can be prepared by conventional techniques.

Further, it can also be made into any product of tablets, capsules, injections, granules, powders, suppositories, pills, creams, pastes, gels, powders, oral solutions, inhalants, suspensions, dry suspensions, patches and lotions.

Further, based on the above, it can also form with any substance such as a pharmaceutically acceptable carrier or adjuvant or excipient to be a mixture.

All the compounds disclosed herein and mixtures, compositions thereof can be administered to a body via any route of administration. The route of administration can be oral, intravenous, intramuscular, subcutaneous, rectal, vaginal, sublingual, nasal inhalation, oral inhalation, eye drops, or topical or systemic transdermal administration.

All compounds disclosed herein and mixtures, compositions, etc. thereof can be formulated into a single dose, which contains the active compound disclosed herein and carriers, excipients, etc., and the dosage form can be tablets, capsules, injections, granules, powders, suppositories, pills, creams, pastes, gels, powders, oral solutions, inhalants, suspensions, dry suspensions, patches and lotions, etc. These dosage forms may contain ingredients commonly used in pharmaceutical preparations, such as diluents, absorbents, wetting agents, binders, disintegrants, colorants, pH adjusters, antioxidants, bacteriostatic agents, isotonicity adjusters, anti-sticking agent, etc.

Formulations for the dosage forms described above are publicly available such as Remington: The Science and Practice of Pharmacy, 21st Ed., Lippincott Williams & Wilkins, 2006 and Rowe, Raymond C. Handbook of Pharmaceutical Excipients, Chicago, Pharmaceutical Press Published in 2005. Thus, it can be easily prepared by those skilled in the art.

Different dosages can be selected according to the nature and intensity of the disease, and according to the age, sex, body weight, route of administration of the patient. The dosage of the compounds disclosed herein can be 0.01 to 500 mg/kg per day, preferably 1-100 mg/kg per day, which can be administered in single or multiple doses.

Those skilled in the art will understand that as all the compounds disclosed herein and mixtures, compositions, etc. thereof, the medical applications are the typical applications, especially for preventing or treating respiratory syncytial virus infection.

The novel compound can be used for the treatment and prevention of RSV infection by inhibiting the production or secretion of respiratory syncytial virus (RSV). Specific embodiments of the present disclosure have been described above. It should be understood that the present disclosure is not limited to the specific embodiments, and those skilled in the art can make any deformations or modifications within the scope of the claims, which do not affect the essential content of the present disclosure.

The invention claimed is:

1. A compound of formula I or a pharmaceutically acceptable salt or solvate thereof,

I

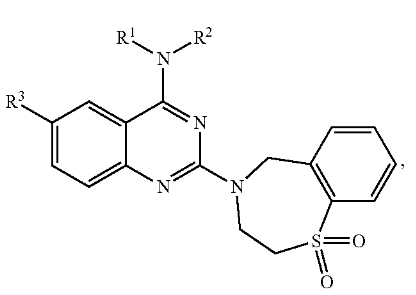

wherein:

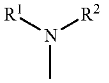

is selected from the group consisting of

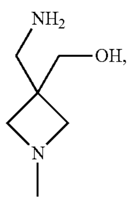

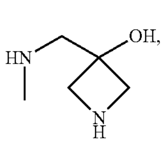

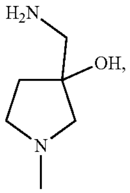

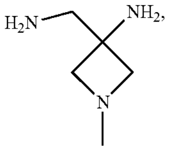

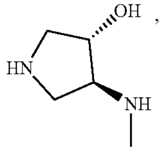

, and

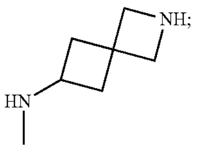

$R^3$ is methyl.

2. The compound according to claim 1, or a pharmaceutically acceptable salt or solvate thereof, wherein the compound is selected from the group consisting

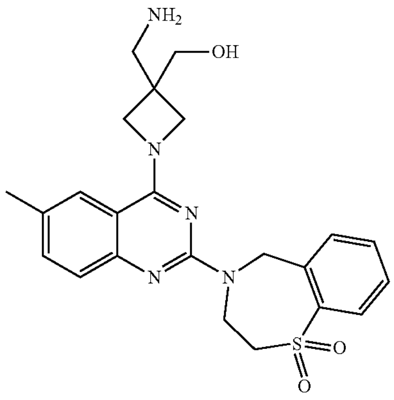

,

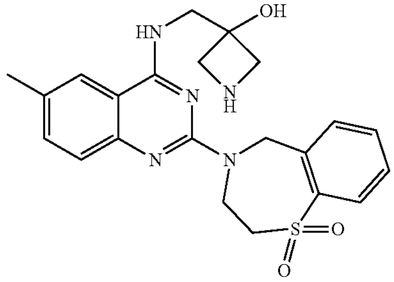

,

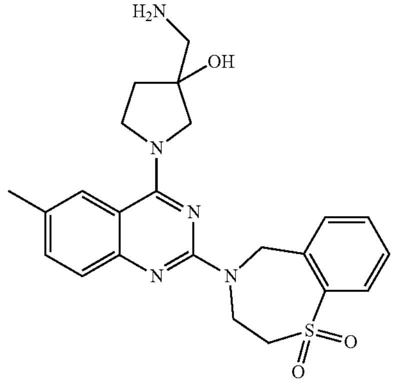

,

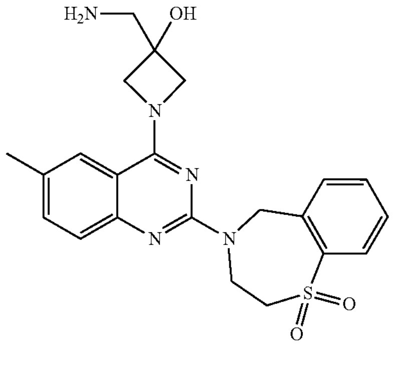

,

-continued

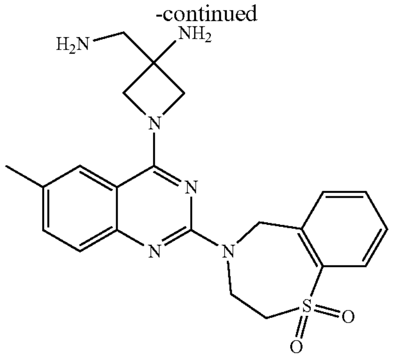

,

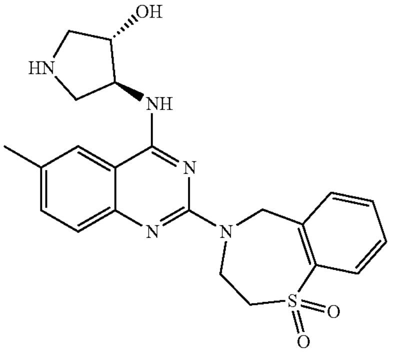

, and

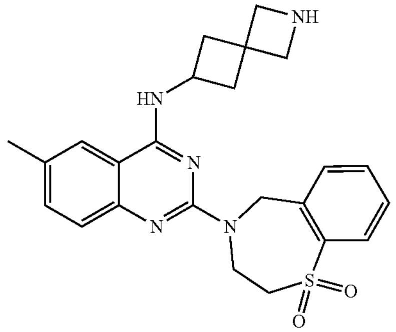

.

3. A pharmaceutical composition, comprising a compound according to claim 1 or a pharmaceutically acceptable salt or solvate thereof.

4. A method for treating a respiratory syncytial virus infection, comprising a step of administering to a subject in need thereof a therapeutically effective amount of the pharmaceutical composition according to claim 1.

5. A compound of formula I-1 or a pharmaceutically acceptable salt or solvate thereof:

I-1

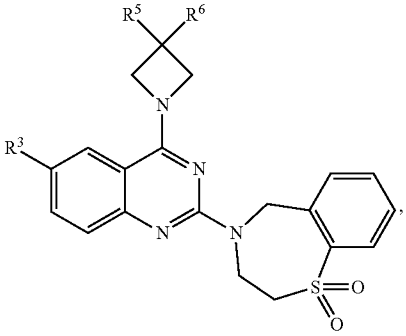

, wherein:

$R^3$ is difluoromethyl, $R^5$ and $R^6$ are each independently selected from hydrogen, amino, and $C_{1-2}$ alkyl, wherein the $C_{1-2}$ alkyl is unsubstituted or substituted with hydroxy or amino, and $R^5$ and $R^6$ are not both hydrogen.

6. The compound according to claim 5, or a pharmaceutically acceptable salt or solvate thereof, wherein the compound is selected from the group consisting

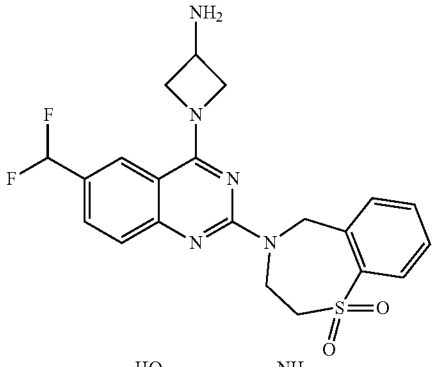

and

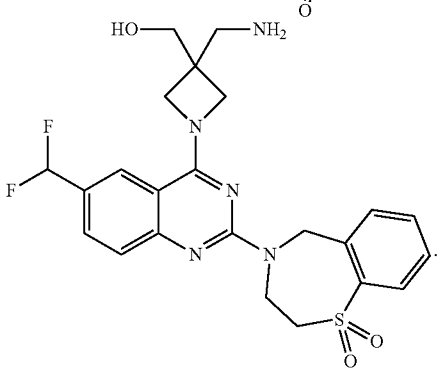

7. A pharmaceutical composition, comprising a compound according to claim 5 or a pharmaceutically acceptable salt or solvate thereof.

8. A method for treating a respiratory syncytial virus infection, comprising a step of administering to a subject in need thereof a therapeutically effective amount of the pharmaceutical composition according to claim 5.

9. A compound of following formula:

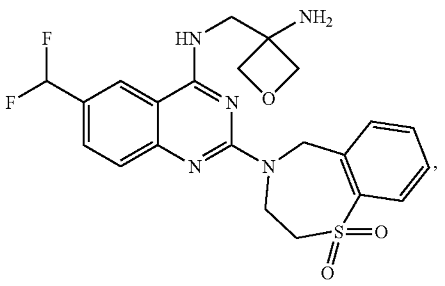 [SMILES: NC1(CNc2nc(N3CCS(=O)(=O)c4ccccc4C3)nc3ccc(C(F)F)cc23)COC1]

or a pharmaceutically acceptable salt or solvate thereof.

10. A pharmaceutical composition, comprising a compound according to claim 9 or a pharmaceutically acceptable salt or solvate thereof.

11. A method for treating a respiratory syncytial virus infection, comprising a step of administering to a subject in need thereof a therapeutically effective amount of the pharmaceutical composition according to claim 9.

* * * * *